US010786483B2

(12) United States Patent
Klein et al.

(10) Patent No.: US 10,786,483 B2
(45) Date of Patent: Sep. 29, 2020

(54) TUMESCENT CONTRAVENOM DRUG DELIVERY

(71) Applicant: HK Pharma, San Clemente, CA (US)

(72) Inventors: Jeffrey Alan Klein, San Juan Capistrano, CA (US); Paytra Alan Klein, Newport Beach, CA (US); Bram Alan Klein, Newport Beach, CA (US)

(73) Assignee: HK PHARMA, San Clemente, CA (US)

( * ) Notice: Subject to any disclaimer, the term of this patent is extended or adjusted under 35 U.S.C. 154(b) by 0 days.

(21) Appl. No.: 15/449,488

(22) Filed: Mar. 3, 2017

(65) Prior Publication Data

US 2017/0252324 A1    Sep. 7, 2017

Related U.S. Application Data

(60) Provisional application No. 62/303,647, filed on Mar. 4, 2016, provisional application No. 62/308,673, filed on Mar. 15, 2016.

(51) Int. Cl.

| | | |
|---|---|---|
| A61K 31/46 | (2006.01) | |
| A61K 9/00 | (2006.01) | |
| A61K 47/02 | (2006.01) | |
| A61K 31/404 | (2006.01) | |
| A61K 9/08 | (2006.01) | |
| A61K 31/137 | (2006.01) | |
| A61K 31/167 | (2006.01) | |
| A61K 45/06 | (2006.01) | |
| A61M 5/145 | (2006.01) | |
| A61M 5/178 | (2006.01) | |

(52) U.S. Cl.
CPC .......... *A61K 31/404* (2013.01); *A61K 9/0019* (2013.01); *A61K 9/08* (2013.01); *A61K 31/137* (2013.01); *A61K 31/167* (2013.01); *A61K 45/06* (2013.01); *A61K 47/02* (2013.01); *A61M 5/1452* (2013.01); *A61M 5/178* (2013.01)

(58) Field of Classification Search
CPC .......... A61K 31/46; A61K 9/00; A61K 47/02
See application file for complete search history.

(56) References Cited

U.S. PATENT DOCUMENTS

| | | | |
|---|---|---|---|
| 5,543,149 A | 8/1996 | Rubin | |
| 8,105,310 B2 * | 1/2012 | Klein | A61M 5/158 604/164.01 |
| 2003/0225074 A1 * | 12/2003 | Cheng | C07D 473/36 514/227.8 |
| 2008/0125354 A1 * | 5/2008 | Fields | A61K 31/4035 514/20.1 |
| 2013/0289470 A1 | 10/2013 | Cherif Zahar | |
| 2017/0354642 A1 * | 12/2017 | Lewin | A61K 38/57 |

FOREIGN PATENT DOCUMENTS

| | | |
|---|---|---|
| DE | 20 2006 016229 U1 | 3/2007 |
| WO | WO 2007/149343 A2 | 12/2007 |
| WO | WO 2008/064393 A1 | 6/2008 |

OTHER PUBLICATIONS

Awai, L.E. and Mekori, Y.A. 1984 "Insect Sting Anaphylaxis and Beta-Adrenergic Blockade: A Relative Contraindication" *Annals of Allergy* 53(1): 48-49 (Abstract).
Bonifazi 2005 "Prevention and treatment of hymenoptera venom allergy: guidelines for clinical practice" *Allergy* 60: 1459-1470.
Butterwick K.J. et al. 1999 "Lidocaine levels during the first two hours of infiltration of dilute anesthetic solution for tumescent liposuction: rapid versus slow delivery" *Dermatol Surg* 25(9): 681-685.
De Luca, D. et al. 2012 "Ex vivo effect of varespladib on secretory phospholipase A2 alveolar activity in infants with ARDS" *Plos One* 7(10: e47066.
Fernandez-Patron, C. and Leung, D. 2015 "Emergence of a metalloproteinase/ phospholipase A2 axis of systemic inflammation" *Metalloproteinases Med* 2: 29-38.
ATI Nursing Education 2015 "Intravenous Therapy" downloaded from the internet on May 9, 2017 from http://web.archive.org/web/20150416041119/https://atitesting.com/ati_next_gen/skillsmodules/content/iv-therapy/equipment/iv-solutions.html (in 3 pages).
Klein, J.A. and Jeske, D.R. 2016 "Estimated Maximal Safe Dosages of Tumescent Lidocaine" *Anesthesia Analgesia* 122: 1350-1359.
Marcussi, S. et al. 2007 "Snake Venom Phospholipase $A_2$ Inhibitors: Medicinal Chemistry and Therapeutic Potential" *Current Topics in Medicinal Chemistry* vol. 7 (in 15 pages).
Sigma-Aldrich 2015 "Papain, product data sheet" downloaded May 5, 2017 from the internet at: https://web.archive.org/web/20150429101328/http://www.sigmaaldrich.com:80/life-science/metabolomics/enzyme-explore/analtical-enzymes/papain.html (in 3 pages).
Samy, R. P. et al. 2012 "Therapeutic application of natural inhibitors against snake venom phospholipase A2" *Bioinformation* 8(1): 048-057.
Toogood, J.H. 1987 "Beta-blocker therapy and the risk of anaphylaxis" *CMAJ* 136: 929-933.

\* cited by examiner

*Primary Examiner* — Zohreh A Fay
(74) *Attorney, Agent, or Firm* — Knobbe, Martens, Olson & Bear, LLP

(57) ABSTRACT

A tumescent contravenom solution including: (a) a vasoconstrictor, (b) a physiological crystalloid solution, and (c) optionally a contravenom agent that neutralizes tissue toxic enzymes present in a venom and/or a drug that impairs or paralyzes lymphatic smooth muscle function and impairs lymphatic transport of venom. Also described are methods of treating an envenomation in a subject, and a kit for performing the method of treating an envenomation.

20 Claims, 8 Drawing Sheets

TUMESCENT CONTRAVENOM DRUG DELIVERY

RELATED APPLICATIONS

This application claims the benefit of U.S. Provisional Application No. 62/303,647, filed Mar. 4, 2016 and U.S. Provisional Application No. 62/308,673, filed Mar. 15, 2016, both of which are hereby incorporated by reference in their entireties.

BACKGROUND

Disclosed are methods of Tumescent ContraVenom Delivery (TCVD), a drug delivery technique consisting of subcutaneous and/or intramuscular infiltration of a relatively large volume of a dilute vasoconstrictor solution containing contravenom drug(s) within and around the site of an envenomation.

The World Health Organization lists snakebite as a neglected disease. Snakebites predominantly affect poor rural populations in medically indigent countries, often in remote and resource-limited communities without access to basic medical care.

Many first aid measures have been recommended for snakebites. None are dependably effective. The standard of care for animal envenomation (snakebite, insect bites, etc.) is hospitalization and intravenous antivenom infusions.

Current first aid recommendations include: 1) keep the victim calm to minimize heart rate and cardiac output, 2) wrapping of the affected extremity with mild pressure dressing in order to inhibit lymphatic fluid flow while maintaining adequate arterial circulation, 3) transport the victim to a hospital as soon as possible. Pre-hospital first aid treatment of animal envenomation (e.g. snakebites) is rudimentary and dependent on the effectiveness of the first aid provider. Current first aid recommendations focus delaying venom absorption, using pressure bandage and immobilization, while avoiding the dangers of tourniquets that impair arterial circulation. Recognition of the importance of lymphatic transport of venom has inspired first aid procedures for snakebite aimed at reducing lymphatic flow rates by mechanically compressing the lymphatic vessels in an affected limb.

There is a need for a safe and inexpensive pre-hospital treatment for venomous bites and stings that is inexpensive, does not require refrigeration, has a long shelf-life, is simple to administer by non-medical personal and can significantly delay and reduce systemic neurologic and hematologic toxicity and reduce local tissue necrosis associated with snakebites.

Antivenom is a biological drug product produced by injecting dilute venom into an animal (e.g., a horse) to induce immunoglobulin against the venom, which is then used to treat venomous bites or stings. The first snake antivenom was developed in 1895 for treating envenomation by the Indian cobra. There has been no new method of treating snakebites in 120 years.

Antivenom is expensive, typically requires refrigeration, is not readily available in remote or rural communities where snakebite envenomation most commonly occur. Antivenom must be given intravenously by trained and experienced medical personal. Antivenom can have serious side effects such as anaphylaxis or seru sickness.

Venom toxicity can be the result of direct action of the toxin on tissue (dose related) or the result of indirect action (possibly not dose related). It is well known that the direct toxic effect of venom is proportional to total dose and rate of systemic absorption of venom. "Toxicity as a function of dose" of venom is a well-known pharmacodynamic concept. Similarly, "toxicity as a function of absorption rate" for a given dose of venom is a well-known pharmacokinetic concept.

Experimentally, snake venom toxicity is also a function of concentration (Pakmanee, N. et al. 1998 "Envenomation of mice by Thai cobra (*Naja kaouthia*) venom: tolerable venom concentration and exposure time" *Toxicon* 36(5): 809-812). In experimental injections of cobra venom in mice, it has been shown that venom dilution prior to injection allows mice to survive longer and tolerate higher dosages.

SUMMARY

Some embodiments relate to a tumescent contravenom solution comprising:
(a) a vasoconstrictor, and
(b) a physiological crystalloid solution.

In some embodiments, the tumescent contravenom solution comprises a contravenom agent that neutralizes tissue toxic enzymes present in a venom.

In some embodiments, the contravenom is selected from the group consisting of a proteinase inhibitor, a metalloproteinase chelating agent, a phospholipase A2 inhibitor, a cellular receptor site blocker, a platelet activator and a platelet activation inhibitor.

In some embodiments, the phospholipase A2 inhibitor is Varespladib or a salt thereof.

In some embodiments, the salt of Varespladib is a sodium salt.

In some embodiments, the contravenom neutralizes a venom from an organism selected from the group consisting of a *Cnidarian*, a jellyfish, a sea anemone, a hydra, a mollusk, an annelid, an arthropod, a spider, a scorpion, a centipede, a bee, a wasp, an ant, a tick, a horsefly, an echinoderm, a starfish, a sea urchin, and a venomous vertebrate, including a fish, an amphibian, a snake, a lizard and a mammal.

In some embodiments, the vasoconstrictor is epinephrine.

In some embodiments, the epinephrine is at a concentration of 0.2 to 1.5 mg/L.

In some embodiments, the tumescent contravenom solution comprises a drug that impairs or paralyzes lymphatic smooth muscle function and impairs lymphatic transport of venom.

In some embodiments, the tumescent contravenom solution comprises a local anesthetic.

In some embodiments, the local anesthetic is lidocaine.

In some embodiments, the lidocaine is at a concentration of 0.4 mg/ml to 1.2 mg/ml.

In some embodiments, the tumescent contravenom solution comprises a beta-blocker drug that slows heart rate, thereby limiting systemic distribution of venom.

In some embodiments, the concentration of contravenom agent is diluted by a factor of 2 or more by the physiological crystalloid solution, or wherein a volume used to dissolve a lyophilized powder of the contravenom agent is at least twice a minimal amount required to dissolve the contravenom agent.

In some embodiments, the physiological crystalloid solution is selected from the group consisting of 0.9% physiologic saline and lactated Ringer's solution.

Some embodiments relate to a method of treating an envenomation in a subject comprising locally injecting a tumescent contravenom solution as disclosed herein within and/or around a site of the envenomation.

In some embodiments, the method comprises self-administering of the tumescent contravenom solution by the subject.

In some embodiments, the tumescent contravenom solution is injected subcutaneously or intramuscularly.

In some embodiments, the contravenom solution is injected within 5-10 minutes following the envenomation.

Some embodiments relate to a kit for performing the method according to claim 16 comprising:
(a) a physiological crystalloid solution,
(b) a vasoconstrictor that is either in solid or liquid form,
(c) a hypodermic needle or an infiltration cannula, and
(d) a syringe.

In some embodiments the kit further comprises a contravenom agent and/or a drug that impairs or paralyzes lymphatic smooth muscle function and impairs lymphatic transport of venom.

DETAILED DESCRIPTION

Figure 1:
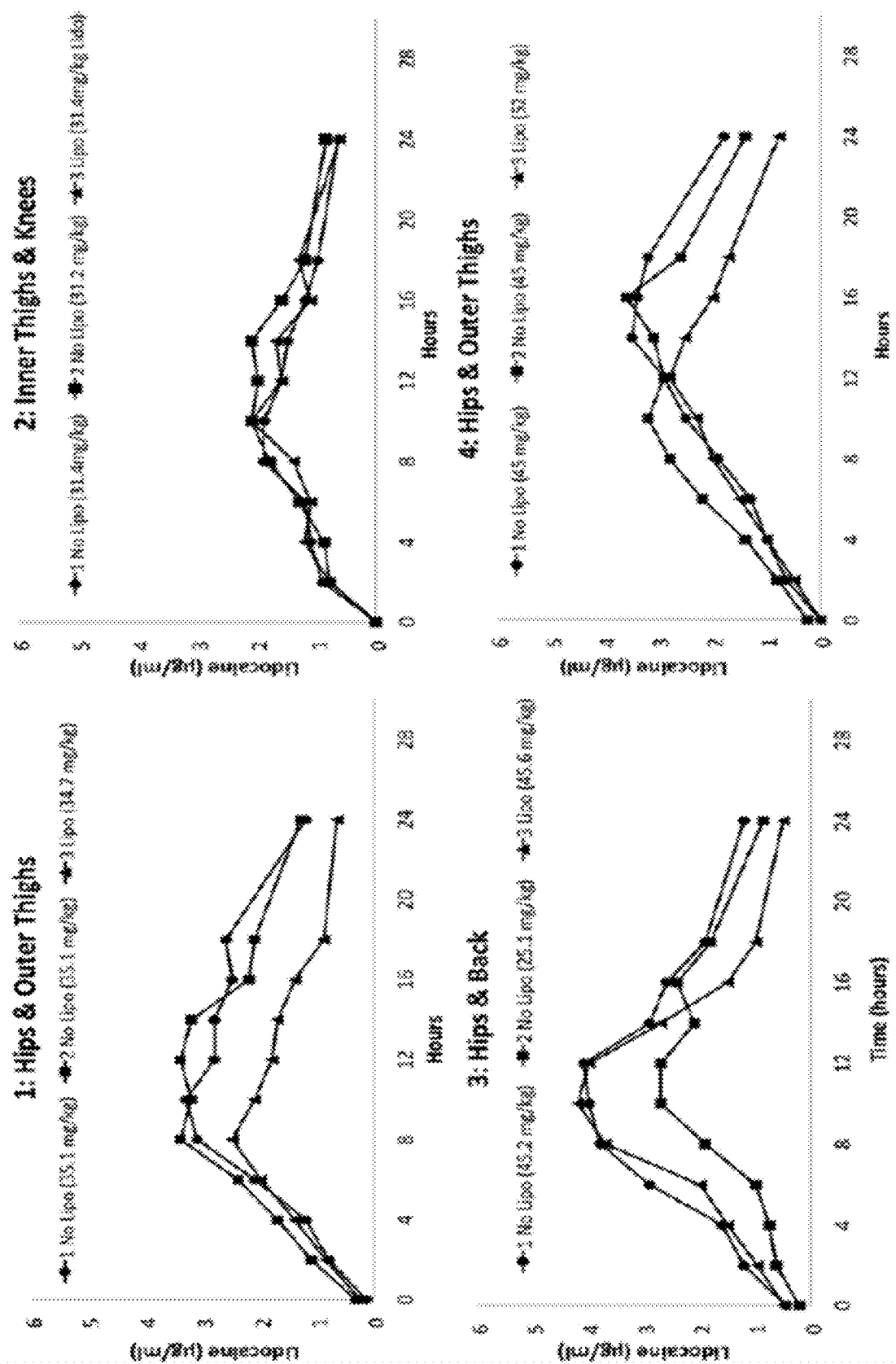
FIG. 1. Serum lidocaine concentrations over time for each of the 14 subjects after subcutaneous infiltration of tumescent lidocaine anesthesia. Subject number and anatomic area of infiltration are presented on the top of each plot. The figure legend presents whether or not liposuction was done after tumescent infiltration indicated by "No Lipo" and "Lipo," respectively, and the tumescent lidocaine dosage (mg/kg).
Figure 1:
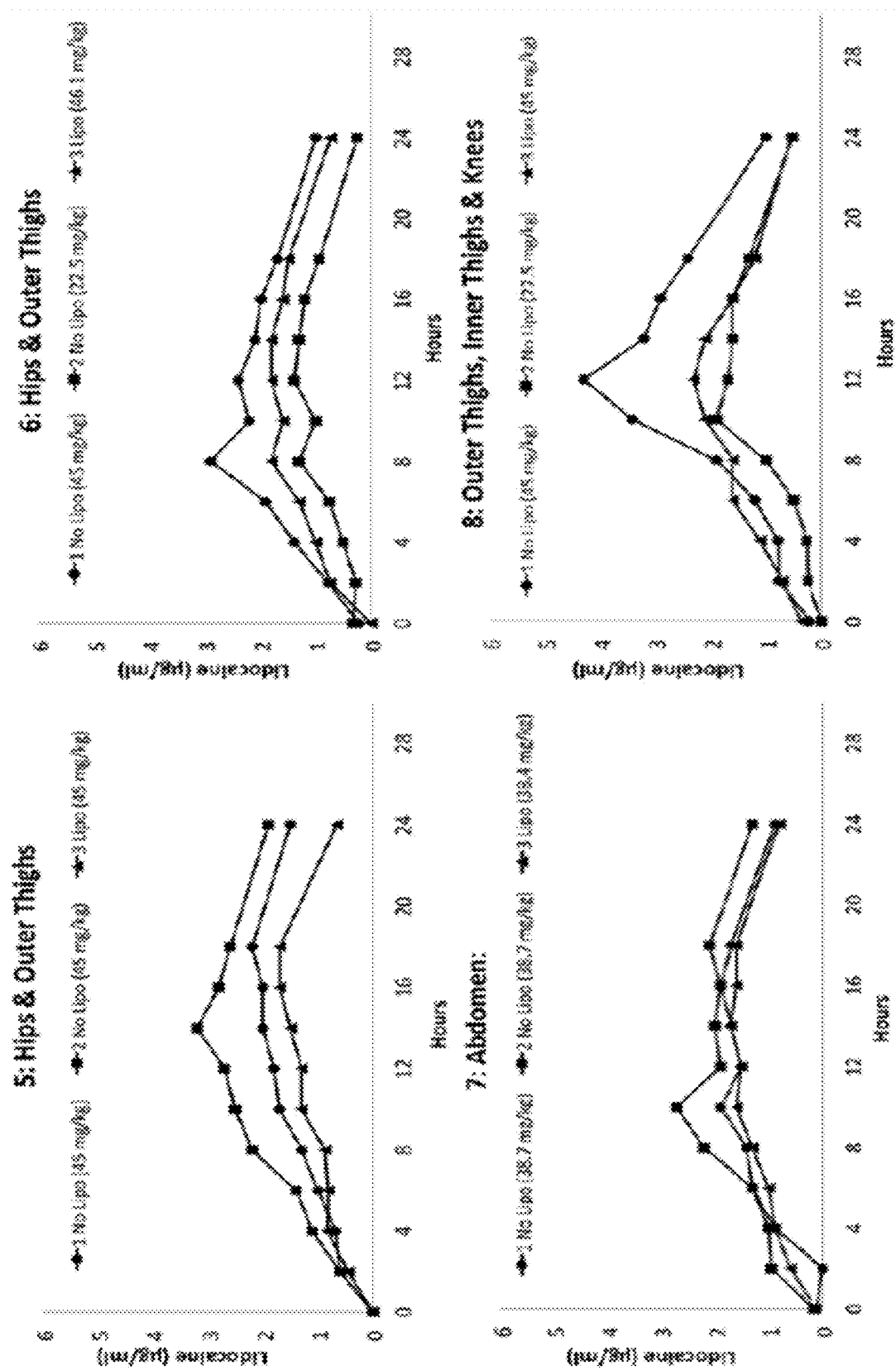
Figure 1:
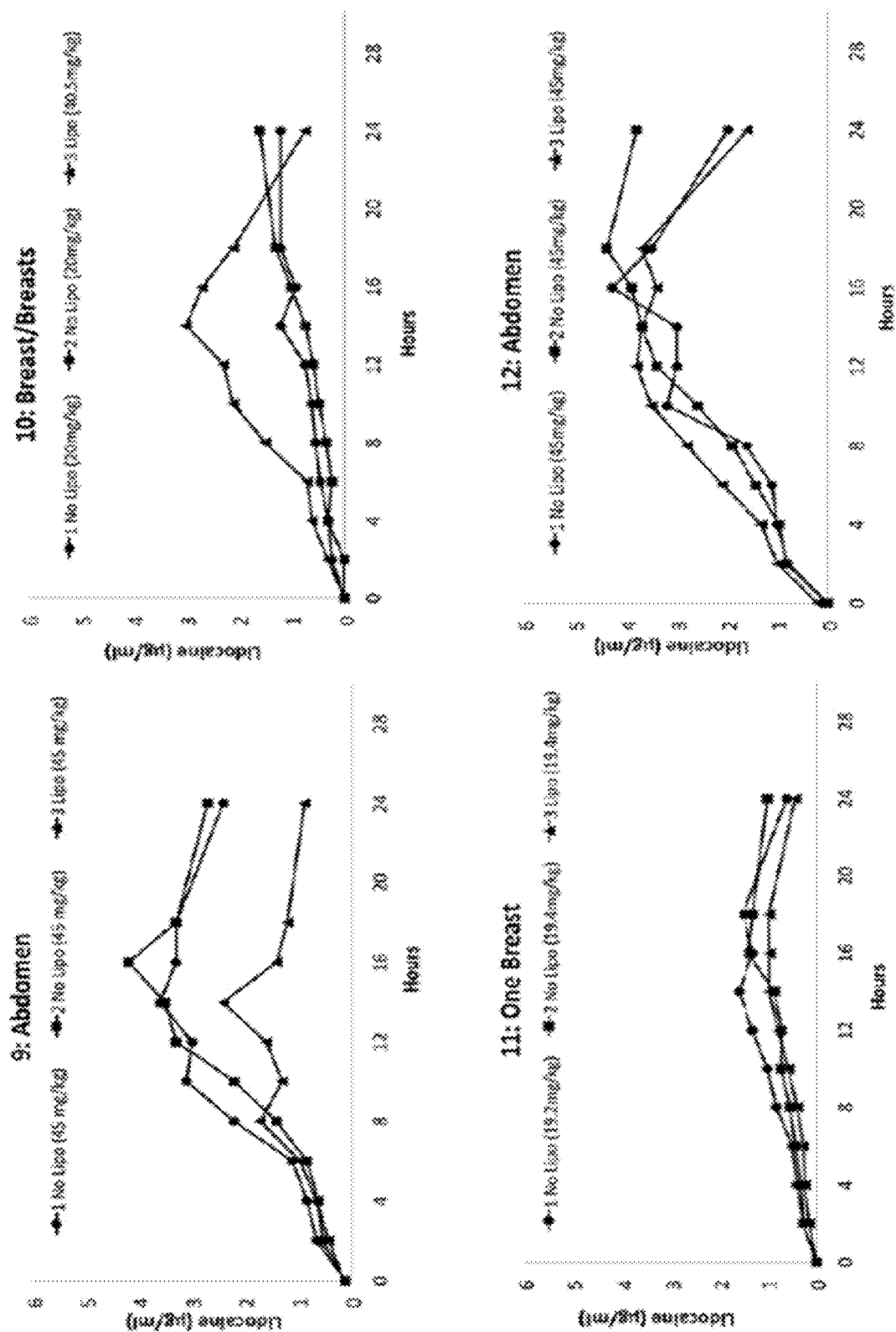
Figure 1:
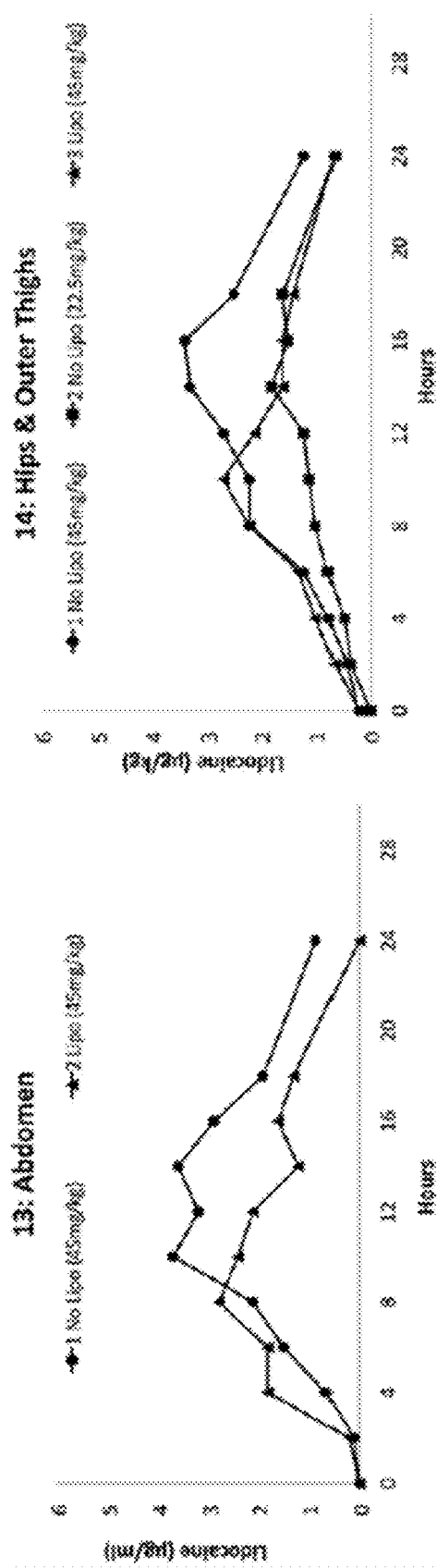

As described in further detail below, the presently claimed embodiments take advantage of the tumescent technique in order to provide brief or prolonged infiltration of a therapeutic contravenom solution. Dilution of venom AFTER a venomous bite or sting is an entirely new concept, which is referred to here as Tumescent Rescue.

There is a need for an improved technique for pre-hospital treatment of animal envenomation that is safe, effective, inexpensive, readily available in remote/rural environments, and simple to administer by a person with minimal training. The current invention, Tumescent ContraVenom (TCV) delivery, has satisfied these criteria in our mouse-model experiments. Direct subcutaneous and intramuscular injection of contravenom agents at or near the site of an envenomation, has not been described.

Contravenom (a neologism) refers to any non-biological drug used to treat venomous snakebites as well as non-biological drugs that treat envenomation by other venomous organisms such as spiders, insects and fish. Contravenom drugs oppose or ameliorate the toxic effects of venom. Examples of contravenoms include proteinase inhibitors, metalloproteinase chelating agents, phospholipase A2 inhibitors, cellular receptor site blockers, platelet activation inhibitors, local anesthetics, vasoconstrictors, drugs that impair, impede, or paralyze smooth muscle function, and physiologic crystalloid solutions such as 0.9% physiologic saline and lactated Ringer's solution. Dilution per se reduces the toxicity of a toxin or venom.

Proteinase Inhibitors

Snake venom often contains proteases. Snake venom proteases inhibit the natural function of victim proteins (enzymes). In some instances, snake venom contains protease inhibitors, such as proteases that interfere with normal blood coagulation processes. Protease inhibitors are potential therapeutic drugs that can neutralize snake venom proteases. There are numerous types of host proteins that can be adversely affected by snake venom proteases. Potential therapeutic proteases inhibitors to counteract venom proteases are also numerous. Whether or not a protease inhibitor can function as a contravenom drug depends on safety and effectiveness of the protease inhibitor drug, on the specificity of the protease inhibitor, on the solubility of the protease inhibitor in a tumescent solution, on potential drug interactions with other ingredients in the tumescent contravenom solution and compatibility with host tissues (Matsui T et al. 2000 *Biochim Biophys Acta* 1477:146-56)

Metalloproteinase Chelating Agents

Metalloproteinases are among the most abundant toxins in many Viperidae venoms. Snake venom metalloproteinases (SVMPs) are the primary factors responsible for hemorrhage and may also interfere with the hemostatic system, thus facilitating loss of blood from the vasculature of the prey. SVMPs are phylogenetically most closely related to mammalian ADAM (a disintegrin and metalloproteinase) and ADAMTS (ADAM with thrombospondin type-1 motif) family of proteins and, together with them, constitute the M12B clan of metalloendopeptidases. Large SVMPs, referred to as the P-III class of SVMPs, have a modular architecture with multiple non-catalytic domains. The P-III SVMPs are characterized by higher hemorrhagic and more diverse biological activities than the P-I class of SVMPs, which only have a catalytic domain.

The biochemical characteristics of hemorrhagic metalloproteinases isolated from snake venoms cause local tissue damage characteristic of crotaline and viperine snake envenomations. Venom metalloproteinases differ in their domain structure. Some enzymes comprise only a metalloproteinase domain, others have disintegrin-like and high cysteine domains and others present, besides these domains, an additional lectin-like subunit. All of them are zinc-dependent enzymes with highly similar zinc binding environments. Some metalloproteinases induce hemorrhage by directly affecting mostly capillary blood vessels. It is suggested that hemorrhagic enzymes cleave, in a highly selective fashion, key peptide bonds of basement membrane components, thereby affecting the interaction between basement membrane and endothelial cells. As a consequence, these cells undergo a series of morphological and functional alterations in vivo, probably associated with biophysical hemodynamic factors such as tangential fluid shear stress.

Eventually, gaps are formed in endothelial cells through which extravasation occurs. In addition to hemorrhage, venom metalloproteinases induce skeletal muscle damage, myonecrosis, which seems to be secondary to the ischemia that ensues in muscle tissue as a consequence of bleeding and reduced perfusion. Microvessel disruption by metalloproteinases also impairs skeletal muscle regeneration, being therefore responsible of fibrosis and permanent tissue loss after snakebites. Moreover, venom metalloproteinases participate in the degradation of extracellular matrix components and play a relevant role in the prominent local inflammatory response that characterizes snakebite envenomations, since they induce edema, activate endogenous matrix metalloproteinases (MMPs) and are capable of releasing TNF-alpha from its membrane-bound precursor. Owing to their protagonic role in the pathogenesis of local tissue damage, venom metalloproteinases constitute relevant targets for natural and synthetic inhibitors which may neutralize effects of the venom metalloproteinases.

Phospholipase A2 Inhibitors

Venom-derived, secreted phospholipases A2 (sPLA2s) fall into four major sub-Types conventionally referred to as Types 1, 2, 3 and 4. Types 1 and 2 sPLA2s are found in the venoms of snakes. Type 3 sPLA2 enzymes are structurally unique and are found only in the venoms of the Gila Monster (*Heloderma suspectum*) and the Mexican Beaded Lizard (*Heloderma horridum horridum*), and venom of the bee *Apis mellifera*. Type 4 sPLA2 are very small polypeptides of between 40 and 80 residues that are secreted in the venom of some marine cone snails of the genus *Conus*.

PLA2 enzymes are commonly found in mammalian tissues as well as arachnid, insect and snake venom. Venom from both snakes and insects is largely composed of melittin, which is a stimulant of PLA2. Due to the increased presence and activity of PLA2 resulting from a snake or insect bite, arachidonic acid is released from the phospholipid membrane disproportionately. As a result, inflammation and pain occur at the site. There are also prokaryotic A2 phospholipases.

Phospholipases A2 (PLA2s) are commonly found in snake venoms from Viperidae, Hydrophidae and Elaphidae families and have been extensively studied due to their pharmacological and physiopathological effects in living organisms.

The peripheral nervous system is particularly susceptible to attack by neurotoxins because the terminal parts of the motor axons and the terminal boutons are not protected by either a blood-axon barrier or a perineurium. The nerve terminals are also a long distance from the parent cell body and, accordingly, rely on an extremely efficient system of both anterograde and retrograde transport for their maintenance. Neurotoxic sPLA2s are presynaptically active, targeting the motor nerve terminal and the terminal part of the motor axon. They do not bind to or block junctional ACh receptors (although at high concentrations they may stablilize the ACh receptor in its desensitized state). Most neurotoxic PLA2s are also myotoxic.

A variety of natural and artificial snake venom phospholipase A2 inhibitors having therapeutic potential against venom phospholipase A2s are known (Marcussi et al. 2007 "Snake Venom Phospholipase A2 Inhibitors: Medicinal Chemistry and Therapeutic Potential" *Current Topics in Medicinal Chemistry*, 7(8): 743-56. Phospholipase A2 inhibitors are administered at a concentration that exceeds the IC50 value, e.g., 2×-10× the IC50 value.

Varespladib Administration Via Tumescent Delivery

In some embodiments, Varespladib (LY315920) or methyl varespladib is used as a contravenom drug for tumescent delivery for the neutralization of a snake venom. Varespladib (LY315920) is effective at neutralizing a wide variety of snake venoms in mice. Varespladib (LY315920) exhibits a significant inhibitory effect on sPLA2 activity in serum from various species including rat, rabbit, guinea pig and human with IC50 of 8.1 nM, 5.0 nM, 3.2 nM and 6.2 nM, respectively. Varespladib is administered at a concentration of 2×-10× the IC50 value. Varespladib is particularly effective in neutralizing venom in a subject when administered via the tumescent contravenom delivery technique disclosed herein.

The breadth and potency of Varespladib and methyl-varespladib against 28 medically important venoms from six continents are summarized in Table A and in Lewin et al. (2016 *Toxins* 8: 248).

TABLE A

Varespladib and methyl-varespladib have breadth and potency against 28 medically important venoms from six continents.

| Venom | Geographic Range | Varespladib IC50 mM | Me-Varespladib IC50 mM |
|---|---|---|---|
| Bee Venom | Worldwide | 13.25 | *Indeterminate |
| *Acanthophis antarcticus* (Common death adder) | Australia/PNG | 0.0006 | Not tested |
| *Agkistrodon blomhoffii* brevicaudus (Mamushi) | SE Asia Japan | 0.0005 | 0.04 |
| *Agkistrodon contortrix* (Copperhead) | N. America | 0.0002 | Not tested |
| *Agkistrodon piscivorus* (Cottonmouth) | N. America | 0.0003 | Not tested |
| *Bitis gabonica* (Gaboon viper) | Africa | 0.0003 | Not tested |
| *Bothrops asper* (Fer-de-lance) | S. America | 0.0001 | Not tested |
| *Bothrops jararaca* (Jararaca) | S. America | 0.0002 | Not tested |
| *Bungarus caeruleus* (Common krait) | India/Asia | 0.0001 | 0.02 |
| *Bungarus fasciatus* (Banded krait) | India/Asia | 0.00003 | 0.01 |
| *Calloselasma rhodostoma* (Malayan pit viper) | SE Asia | 0.002 | Not tested |
| *Crotalus adamanteus* (Eastern diamondback rattlesnake) | N. America | 0.0002 | 0.02 |
| *Crotalus atrox* (Western diamondback rattlesnake) | N. America | 0.0003 | 0.04 |
| *Crotalus durissus terrificus* (South American rattlesnake) | S. America | 0.005 | 0.26 |
| *Crotalus scutulatus scutulatus* (Mojave green rattlesnake) | N. America | 0.002 | 0.21 |
| *Dendroaspis polylepis* (Black mamba) | Africa | 0.00003 | 0.02 |
| *Echis carinatus* (Saw-scaled viper) | India/Pakistan | 0.00006 | 0.009 |
| *Laticauda semifasciata* (Banded sea krait) | Pacific Ocean | 0.00006 | 0.02 |
| *Micrurus fulvius* (Eastern coral snake) | N. America | 0.001 | 0.08 |
| *Naja naja atra* (Chinese cobra) | China/Taiwan | 0.0008 | 0.01 |
| *Naja naja kaouthia* (Monocled cobra) | India/Asia | 0.00005 | 0.02 |

TABLE A-continued

Varespladib and methyl-varespladib have breadth and potency against 28 medically important venoms from six continents.

| Venom | Geographic Range | Varespladib IC50 mM | Me-Varespladib IC50 mM |
|---|---|---|---|
| *Naja naja naja* (Spectacled or Indian cobra) | India | 0.001 | 0.02 |
| *Notechis scutatus scutatus* (Tiger snake) | Australia | 0.00006 | 0.03 |
| *Ophiophagus hannah* (King cobra) | India/Asia | 0.003 | 0.001 |
| *Oxyuranus scutellatus* (Coastal taipan) | Australia/PNG | 0.001 | 0.01 |
| *Pseudechis australis* (Mulga snake) | Australia | 0.003 | 0.09 |
| *Trimersurus elegans* (Elegant pit viper) | SE Asia | 0.0007 | Not tested |
| *Vipera berus* (Common European adder) | Europe/Asia | 0.00002 | 0.03 |
| *Vipera russelli* (Russell's viper) | India/Asia | 0.0006 | 0.02 |

(Vipers n = 15, Elapids n = 13) in vitro (Common English names are in parentheses). IC50 (μM) were calculated using chromogenic assays for sPLA2 inhibition; R-square for dose response curves 0.96 0.04 (95% C.I. 0.94-0.98). While demonstrating high degrees of potency against snake venoms, neither varespladib nor methyl-varespladib showed high degrees of potency against bee venom sPLA2 (positive control).
*Indeterminate = No apparent effect.
PNG, Papua New Guinea;
N., North;
S., South;
SE, South East.

Varespladib sodium (also known as A-001, previously LY315920 and S-5920) is a sodium salt of varespladib. Varespladib (LY315920) is an inhibitor of the IIa, V, and X isoforms of secretory phospholipase A2 (sPLA2). The molecule acts as an anti-inflammatory agent by disrupting the first step of the arachidonic acid pathway of inflammation. Varespladib is off-patent for its original clinical application. It has never received FDA approval due to inadequate efficacy as an antiinflammatory and as a cardiovascular drug.

Traditional antivenoms are immunologic or biological drugs that reduce the toxicity of venom. Traditional immunologic or biological antivenoms are not heat stable, are very expensive and have a rather short shelf life. In contrast, Varespladib is neither an immunological drug nor a biological drug. As such, it is heat stable and has a relatively long shelf life.

Cellular Receptor Site Blockers

Direct interaction of snake venom proteins with cells may involve a variety of mechanisms that result in diverse cellular responses leading to the activation or blocking of physiological functions of the cell. The most important cellular receptors responsible for cell/extracellular matrix (ECM) interaction are integrins. Viper venoms contain antagonists of integrins, which were structurally classified as disintegrins and C-type lectin proteins (CLP). The disintegrin family binds certain types of integrins through specific motifs recognized as a RGD tri-peptide structurally localized on an integrin-binding loop. Cellular receptor site blockers that block interaction of venom proteins with integrins may be used as a contravenoms.

Platelets were the first cells investigated in context of snake venom disintegrins. They express αIIbβ3 integrin, which binds fibrinogen through an RGD motif. The majority of discovered snake venom disintegrins contain an RGD or related motif in the active site and they potently block activity of these thrombocytes. Leukocytes express receptors, which are targeted by disintegrins. Interaction of RGD-monomeric disintegrins with neutrophils appears to be associated with binding to the αMβ2 integrin (Mac-1). Snake venom disintegrin research has been extensively performed with endothelial cells. These major vessel wall cells are exposed to the blood stream and are on the first line of attack of snake venom components during envenomation.

C-type lectin proteins (abbreviated: CLPs, CTLs or Snaclecs) belong to another family of snake venom proteins, which have also been characterized as integrin-binding molecules. They are broadly spread among different species of vipers, having diverse effects on the circulatory system of the victim. Major attention has been committed to platelets as a potential target for CLPs, although some proteins in the blood coagulation system such as factors IX/X or von Willebrand factor were also affected by these snake venom compounds. The binding of CLPs to certain receptors expressed on the platelet surface may result in an agonistic or antagonistic effect on thrombosis (Clemetson K J. 2010 "Snaclecs (snake C-type lectins) that inhibit or activate platelets by binding to receptors" *Toxicon* 56:1236-46).

Procoagulants and Coagulation Inhibitors

Snake venoms profoundly affect blood coagulation and platelet function, being classified as procoagulants, including factor X activator, prothrombin activator, thrombin-like enzymes and platelet aggregation inducer, and coagulation inhibitors, including fibrinogenolytic enzymes, prothrombin activation inhibitor, Factor X inhibitors, and platelet aggregation inhibitors.

Regarding platelet aggregation inhibitors, many venom components including ADPase, snake venom metalloproteinase (SVMP), phospholipase A2, GPIb and IX binding proteins (i.e., snaclec) and disintegrins have been reported to suppress platelet aggregation in vitro. However, snaclecs and disintegrins affect in vivo hemostasis and cell adhesion in a specific manner. Snaclecs can either induce platelet aggregation through vWF modulation, GPIb, α2β1, CLEC-2 and GPVI binding; or inhibit platelet aggregation via GPIb blockade.

Many snake venom proteins have been isolated that affect platelet plug formation by interacting either with platelet integrins, membrane glycoprotein Ib (GPIb), or plasma von Willebrand factor (VWF). Among them, disintegrins purified from various snake venoms are strong inhibitors of platelet aggregation. Botrocetin and bitiscetin derived from *Bothrops jararaca* and *Bitis arietans* venom, respectively, induce VWF-dependent platelet agglutination in vitro. Several GPIb-binding proteins have also been isolated from snake venoms. Natural or synthetic contravenoms may counter either procoagulation or coagulation inhibitory properties of a venom.

Delayed Lymphatic Transport

Snake venoms contain multiple different large protein molecules that cannot enter the bloodstream by direct absorption across blood-capillary endothelium but are transported by lymphatic vessels and enter vein blood at the thoracic duct. (Saul M E et al. 2011 *Nat Med* 17: 809-11).

Nitric Oxide (NO) Donors, Such as Nitroglycerine or Amyl Nitrite.

NO causes vascular smooth muscle to relax. The result is vasodilation of blood vessels and impairment of lymphatic pumping. NO inhibits lymphatic smooth muscle contraction by stimulating cGMP production, which inhibits $Ca^{2+}$ release and vascular smooth muscle contraction. (Carvajal J A et al. 2000 *J Cell Physiol* 184:409-20).

Calcium Channel Blockers

Verapamil and/or other calcium channel blockers inhibit lymphatic vessel smooth muscle pumping contractions. The percutaneous absorption of nifedipine, a calcium channel blocker, and lidocaine, when applied topically have been shown to impair lymphatic smooth muscle contraction, prolong lymph transit time in rats and increase rat survival time after injection of venom. (Helden D F et al. 2014 *PLoS Negl Trop Dis* 8:e2722).

Tumescent Antivenom or Contravenom Delivery

Tumescent Lidocaine Anesthesia (TLA) consists of lidocaine (≤1 gm/L), epinephrine (≤1 mg/L) and sodium bicarbonate (10 mEq/L) in 0.9% physiologic saline. The subcutaneous infiltration of a relatively large volume of TLA provides profound, long-lasting local anesthesia that permits surgical procedures totally by local anesthesia involving extensive areas of skin and subcutaneous tissues. At a dosage of 28 mg/kg of TLA lidocaine, the risk of mild lidocaine toxicity is 1/5,000,000.

Antivenoms are biologic drugs in the form of antibodies and antibody fragments derived from the serum of hyperimmunized animals, such as horses and sheep. Antivenoms can be delivered in a TLA solution of dilute lidocaine with epinephrine.

Contravenoms (CV) are non-biologic drugs that counteract the toxicity of animal venom. The beneficial effects of a TCV solution can be the result or hydrodynamic (mechanical) forces or chemical interactions.

The volume of a TCV solution can vary from a few milliliters to a liter or more. When a relatively large volume of TCV solution is infiltrated into the subcutaneous and muscular interstitial space, the affected tissue and overlying skin can become tumescent or swollen and firm. The optimal volume of the TCV solution can depend on the characteristics of the venom and anatomic site of the envenomation.

Tumescent ContraVenom (TCV) delivery consists of a TLA tumescent solution containing one or more contravenoms that is injected directly into subcutaneous and muscular tissue in order to neutralize the venom locally and/or delay the absorption of the venom systemically.

Formulation of a Tumescent ContraVenom (TCV) solution, by way of example, can include, but is not limited to, the following constituents:

1) Lidocaine and/or another local anesthetic
2) Epinephrine and/or another vasoconstrictor
3) Nitric oxide (NO) donors such as nitroglycerine or amyl nitrite. NO causes vascular smooth muscle to relax. The result is vasodilation of blood vessels and impairment of lymphatic pumping. NO inhibits lymphatic smooth muscle contraction by stimulating cGMP production, which inhibits Ca2+ release and vascular smooth muscle contraction. (Carvajal J A, Germain A M, Huidobro-Toro J P, Weiner C P. Molecular mechanism of cGMP-mediated smooth muscle relaxation. J Cell Physiol. 2000; 184:409-20).

4) Verapamil and/or other calcium channel blockers that inhibit lymphatic vessel smooth muscle pumping contractions.
5) Chelating agents and enzyme inhibitors that inactive or neutralize venom proteins.
6) Any other drugs that inactivate venom proteins.

Tumescent ContraVenom solutions can:

1) reduce extravasation of serum across blood-capillary endothelium by widespread epinephrine-induced vasoconstriction
2) delay systemic absorption of venom via lymphatic absorption and transport of venom to the thoracic duct and into the systemic circulation by calcium channel blockers that impair lymphatic vascular smooth muscle contractions
3) local and systemic neutralization of cytotoxic venom by impairing the cytotoxic enzymatic effects of venom by drugs with specific chelating, anti-phosphodiesterase, etc., activity.
4) dilute venom and reduce local toxicity.

Local Anesthetics

In some embodiments, the contravenom solution contains a local anesthetic, which has advantageous properties including amelioration of pain, bactericidal properties, and platelet inhibition.

Pain amelioration is advantageous in facilitating local injection of a tumescent contravenom solution at a site of envenomation, in the absence of other medical supplies or medical facilities.

Lidocaine present in the solution can affect platelet function by means of several diverse mechanisms. For example, the release of the phospholipid messenger lysophosphatidate from activated platelets is inhibited by the extracellular application of lidocaine in concentrations injected into surgical wounds. In addition, lidocaine may inhibit platelet aggregation by acting on adenosine diphosphate (ADP). Lidocaine, as well as other local anesthetics, benzocaine and bupivacaine, have been shown to inhibit platelet aggregation induced by ADP. In addition, at concentrations much higher than that required to decrease platelet aggregation, lidocaine inhibits the shape change associated with platelet aggregation. The actual mechanism of platelet inhibition by lidocaine is not known. Not wishing to be bound to a particular theory, however, the concentration of calcium ions may play a role in platelet inhibition by lidocaine and other local anesthetics. Lidocaine and bupivacaine have been shown to inhibit lysophosphate signaling, which induces Ca(2+)-activated Cl— currents. Thus, Lidocaine and bupivacaine may act to impair trans-membrane calcium transportation. In addition, there is evidence that increasing the concentration of calcium decreases the inhibitory effect of lidocaine on platelets.

At safe systemic concentrations (e.g. ≤6 micrograms/ml) lidocaine seems to have no effect on platelet aggregation. However at tissue concentrations achieved after infiltration of a tumescent contravenom solution containing the local anesthetic, there may be significant inhibition of in-vitro platelet aggregation. In-vitro platelet aggregation induced by ADP, epinephrine and collagen is consistently inhibited by lidocaine concentrations equal to or greater than 0.5 mg/ml. The concentration of lidocaine in a tumescent contravenom solution typically ranges from 0.4 mg/ml to 1.2 mg/ml. Furthermore, in-vitro testing of the effect of lidocaine on platelet aggregation has shown that the longer the incubation time with lidocaine, the more efficient the anti-aggregating effect. The local tissue vasoconstriction associated with a tumescent contravenom solution impairs systemic absorption of tumescent lidocaine and dramatically prolongs the local tissue concentrations of lidocaine. Tumescent local anesthesia infiltrated into the site of an envenomation produces very high and prolonged local tissue concentrations of lidocaine and can thereby significantly reduce platelet activation.

The concentration of lidocaine in a tumescent contravenom solution typically ranges from 0.4 mg/ml to 1.2 mg/ml. In some embodiments, combinations of two or more anesthetics may be used. Suitable concentrations of anesthetic may be approximately 30 mg to 40 mg, 40 mg to 50 mg, 50 mg to 60 mg, 60 mg to 70 mg, 70 mg to 80 mg, 80 mg to 90 mg, 90 mg to 100 mg, 100 mg to 200 mg, 200 mg to 300 mg, 300 mg to 400 mg, 400 mg to 500 mg, 500 mg to 600 mg, 600 mg to 700 mg, 700 mg to 800 mg, 800 mg to 900 mg, 900 mg to 1,000 mg, 1,000 mg to 1,100 mg, 1,100 mg to 1,200 mg, 1,200 mg to 1,300 mg, 1,300 mg to 1,400 mg, 1,400 mg to 1,500 mg, and 500 mg to 1,000 mg per liter of solvent.

In some embodiments, the tumescent contravenom solution may comprise additional pharmacological agents, such as, but not limited to, anticonvulsants, stimulants, sedatives, antihistamines, retinoids, corticosteroids, calcium antagonists, calcium channel blockers, chemotherapy agents, prostacyclins, and vasodilators.

Vasoconstrictors

The tumescent contravenom solution comprises a vasoconstrictor component. Not wishing to be bound by a particular theory, the inclusion of a vasoconstrictor serves two functions. The first is to control the otherwise substantial bleeding resulting from the envenomation or injection of the contravenom solution. The second is to control the systemic distribution of the anesthetic and antibiotic components of Tumescent Contravenom solution from the region of the envenomation into the systemic circulation. This helps to concentrate these medications in the area where they are needed for a prolonged period of time, thereby enabling them to exert sufficient contravenom, anesthetic and antibiotic effects at the site of the envenomation. In addition, the use of a vasoconstrictor limits the systemic absorption of other medications, which reduces the risk of systemic toxicity from elevated serum levels of these medications and thereby minimizes the risk of side effects.

In some embodiments, the vasoconstrictor component is epinephrine. Epinephrine may be provided at a concentration of ≤1 mg/L. In some embodiments, epinephrine is present in a concentration of 0.4 to 1.2 mg per liter of solvent. In other embodiments, epinephrine may be present in a concentration of 0.2 to 0.3 mg, 0.3 to 0.4 mg, 0.4 to 0.5 mg, 0.5 to 0.6 mg, 0.6 to 0.7 mg, 0.7 to 0.8 mg, 0.8 to 0.9 mg, 0.9 to 1 mg, 1 to 1.1 mg, 1.1 to 1.2 mg, 1.2 to 1.3 mg, 1.3 to 1.4 mg, or 1.4 to 1.5 mg per liter of solvent. Stability of epinephrine is optimized is solutions of a moderately acidic pH. Tumescent contravenom solutions containing epinephrine may be manufactured with a moderately acidic pH in the range of 3.8 to 5.0 in order to optimize the shelf life of the solution. In order to avoid the burning discomfort associated with the infiltration of an acidic solution, the solution can be neutralized prior to subcutaneous infiltration by the addition of approximately 10-25 mEq of sodium bicarbonate.

Individuals skilled in the art will recognize that vasoconstrictors other than epinephrine can be used in some embodiments of TLAnti. Examples of suitable vasoconstrictors include, but are not limited to, methoxamine, metraminol, ephedrine, noradrenaline, vasopressin, levonordefrin, prostaglandins, thromboxane A2, leukotriene D4, angiotensin II, neuropeptide Y, and endothelin.

In some embodiments, other constituents may optionally be present in the tumescent contravenom solution. In one embodiment, bicarbonate can be present in the solution. This helps to neutralize the otherwise acidic solution and reduce the burning sensation reported by many patients. In other embodiments, the solution can further comprise perfluorocarbons. In some embodiments the solution can further comprise an anti-inflammatory component. Examples of anti-inflammatories include but are not limited to glucocorticoids and NSAIDS. Persons skilled in the art will note that there are a number of potential compounds that can be added to the solution.

Dilution by Physiological Crystalloid Solutions

Dilution decreases the localized tissue necrotic effect of venom. After an envenomation has occurred, the sooner the tumescent rescue can be delivered, the less time there will have been for direct tissue injury to have occurred and for systemic absorption to have occurred. The more time between envenomation and tumescent rescue, the less effective the rescue. This form of tumescent rescue for animal, spider, insect and fish envenomation is novel, unexpected and has not previously been described.

Dilution per se reduces the toxicity of a toxin or venom. Thus, infiltration of a large volume of the tumescent contravenom solution serves to dilute and thereby mitigate toxicity and cellular damage caused by venoms. The most commonly used crystalloid fluid is normal saline, a solution of sodium chloride at 0.9% concentration, which is close to the concentration in the blood (isotonic). Lactated Ringer's solution or Ringer's acetate is another isotonic solution that can be used to provide the bulk volume of the tumescent contravenom solution.

Tumescent Rescue by Dilute Epinephrine following snake envenomation consists of direct subcutaneous and intramuscular infiltration at the site of envenomation of a large volume of dilute vasoconstrictor, e.g., epinephrine (1 mg/L) in normal saline after envenomation has occurred. The combined effects of epinephrine-induced vasoconstriction with decreased local tissue perfusion and significant venom dilution increase survival. Following a subcutaneous or intramuscular injection of a toxin (e.g., venom) or drug, the rate of systemic absorption of the toxin or drug across blood capillary walls and endothelium is perfusion rate-limited. The delayed absorption of venom reduces the peak serum concentration, delays venom-receptor site interactions, and delays the onset of toxic symptoms and may reduce the intensity of toxic symptoms. If the drug is epinephrine, the delayed absorption of epinephrine significantly reduces the incidence of epinephrine-induced tachycardia.

A tumescent rescue solution, consisting of dilute epinephrine in saline, functions as an excellent drug delivery vehicle for treating an envenomation. When any drug is added to a tumescent rescue solution, its rate of systemic absorption is significantly delayed and its local subcutaneous and intramuscular concentration remain high and prolonged, which in turn produces prolonged local drug effects.

A Tumescent ContraVenom solution consists of one or more drugs that counteract, inhibit, neutralize, denature or otherwise block the toxic effects of venom, all dissolved in a solution of tumescent rescue solution containing lidocaine.

Tumescent ContraVenom Delivery (TCVD) is a drug delivery technique consisting of the subcutaneous and intramuscular infiltration of a relatively large volume of a dilute vasoconstrictor solution containing contravenom drugs within and around the site of an envenomation. Specially designed infiltration cannulas and the use of a specially designed infiltration pump (for example a specially designed manual syringe or an electric powered peristaltic pump) facilitate tumescent drug delivery. One embodiment of TCVD consists of contravenom drugs dissolved in a large volume of tumescent lidocaine anesthesia (TLA).

One method of infiltration of local anesthetic is via a blunt tipped infiltration cannula. Infiltrators are known as sprinkler-tip or Klein™ needle infiltrators. These cannula are constructed out of a rigid stainless steel and have one or more apertures, which are typically round or oval, and are distributed about the distal end of the cannula. The apertures are distributed over about 15% to 25% or less than 5.0 cm of the distal end of the cannula needle. These traditional infiltration cannula are intended to be inserted through a small incision in the patient's skin and then moved in and out through the subcutaneous tissue while a dilute solution of contravenom is ejected through the distal apertures. Since the cannula needle is moved in and out, only the distal end (e.g., about 15% to 25%) of the cannula needle may have apertures. Otherwise, fluid may squirt out of the apertures and onto medical professionals when the cannula needle is moved out too much. Such infiltrators typically have a blunt tip and require the placement of a small hole (made by a one mm skin-biopsy punch or a small surgical blade) through which the blunt tipped cannula can be passed.

Another type of infiltration cannula is the sharp tipped tumescent infiltration cannula which is available as: 1) a single long sharp needle similar to a spinal needle, and 2) a group of short sharp hypodermic needles each connected by separate plastic tube to a manifold that distributes Tumescent contravenom solution. The first type of needle is inserted into the region of an envenomation and infiltration proceeds while the needle is continuously moved slowly in and out along paths that radiate from the skin puncture site. A targeted area may be treated with multiple skin punctures. The second type, the group of short sharp needles, consists of a group of individual hypodermic needles each attached to an individual IV extension tube, which are in turn connected to a multi-port manifold which connected to a reservoir (IV bag) of tumescent fluid.

Traditionally, first aid included making local incisions (without infusion of tumescent contravenom) or "tattooing" at the site of the bite, attempts at suctioning venom out of the wound, use of tight bands (tourniquets) around the limb, and/or local application of ice packs. None of the traditional remedies have any proven medical benefit. They should be discouraged as they do more harm than good and delay effective treatment by tumescent contravenom delivery and/or transport to a medical facility. Incision, suction, electric shocks, cryotherapy, or washing the wound are contraindicated as any interference with the wound introduces infection, increases bleeding from the site, and hastens absorption of the venom.

Tumescent lidocaine anesthesia (TLA) consists of the subcutaneous infiltration of relatively large volume of dilute lidocaine (≤1 gm/L), epinephrine (≤1 mg/L), with or without sodium bicarbonate (10 mEq) dissolved in 0.9% physiologic saline. The estimated maximal safe dosages of tumescent lidocaine are 28 mg/kg without liposuction and 45 mg/kg with liposuction (Klein, J. A. and Jeske D. R. 2016 "Estimated maximal safe dosages of tumescent lidocaine" *Anesth Analg* 122: 1350-1359). First published in 1987, TLA has become the worldwide standard of care for liposuction surgery as a result of it exceptional surgical hemostasis and prolonged surgical local anesthesia for 6 to 8 hours. A number of surveys have documented the unrivaled safety record of TLA (Wang G et al. 2015 *Ann Plast Surg* 74:6-11; Klein J A and Jeske D R. 2016 *Anesth Analg* 122:1350-9; and Klein J A 1990 *Dermatol Clin* 8:425-37).

An increasing number of other surgical procedures are now accomplished with TLA (Sleth et al. 2008 *Ann Fr Anesth Reanim* 27:941-944; Orgill 2009 *N Engl J Med* 360:893-901; Gumus, N. 2011 *Ann Burns Fire Disasters* 24:144-148; Haines W Y et al. 2012 *J Vasc Surg* 56:1453-6; and Carlson G W 2005 Breast J 11:100-102).

Tumescent contravenom delivery (TCVD) and tumescent antivenom delivery (TAVD) are analogous. Tumescent contravenom delivery (TCD) involves the tumescent infiltration of non-biological drugs that treat envenomation. Tumescent anti-venom delivery (TAVD) involves the tumescent infiltration of biological antivenom drugs.

Perfusion rate-limited drug absorption explains the efficacy of tumescent drug delivery. When a drug in a vasoconstrictor solution is injected subcutaneously, the rate of systemic drug absorption decreases as the local tissue perfusion decreases. When a large volume of solution consisting of 1 mg/L of epinephrine in normal saline is injected subcutaneously, the local tissue perfusion decreases to a trickle and the skin becomes blanched. Any drug dissolved in this vasoconstrictor solution is absorbed very slowly into the central circulation.

Antivenom therapy typically involves an IV infusion of an animal-derived immunoglobulin. Antivenom is made by the repeated injection of incremental amounts of dilute venom into a domesticated animal and then extracting the animal's venom-specific immunoglobulin.

Disadvantages of antivenom include high cost per vial, the need for multiple vials per patient, short shelf life and refrigeration requirements. The effectiveness of antivenom is often specific to one species of snake within a limited geographic habitat. Antivenom often requires refrigeration, and is often only available in urban medical centers. For victims in rural communities, there is often a dangerous delay in the initiation of antivenom treatment. For many species of venomous animal, effective antivenom simply does not exist. Injecting the serum of a domestic animal into a human can produce serious allergic responses such as an immediate hypersensitivity reaction (anaphylaxis) or a delayed hypersensitivity (serum sickness) reaction. Despite significant limitations, antivenom is usually the only effective treatment for a potentially life-threatening envenomation. There is a need for treatments of venomous bites and stings that are safe, effective, and inexpensive and have a long shelf-life.

Advantages of TCVD

Dilution per se reduces the toxicity of a toxin. TCVD involves the subcutaneous infiltration of a large volume of a dilute solution of drugs that attenuate the effect of venom. Dilution decreases rate of systemic absorption. Dilution decreases intensity of local and systemic toxicity.

A TCVD solution contains dilute tumescent epinephrine that produces blood-capillary vasoconstriction and decreases local tissue perfusion at the site of envenomation. This decreases the rate of systemic absorption of venom from the site of envenomation A TCVD solution may contain dilute tumescent lidocaine, a local anesthetic that provides immediate pain relief at the site of a painful venomous bite or sting. Tumescent lidocaine also inhibits platelet activation, which may reduce the hypercoagulation induced by some venoms. Lidocaine is inexpensive, heat stable and bactericidal A TCVD can contain a beta-blocker drug that slows the heart rate and limits the rate of systemic distribution of venom.

The basic TCVD solution, consisting of 1 mg/L epinephrine in physiologic saline, is inexpensive.

TCVD can be safely administered outside of a hospital setting and can be injected by a lay person who has had little or no health care professional training.

TCVD can be easily administered by non-medical personnel or be self-administered.

The large physical volume of tumescent solution increases interstitial pressure and thus prevents lymphatic drainage of venom into the systemic circulation. The large volume act as a tourniquet by increasing interstitial pressure in tissues proximal to venomous bite, and thus delays systemic absorption.

TCVD can deliver drugs that neutralize tissue-toxic enzymes and thus reduce tissue necrosis at a site of envenomation, for example by chelating venomous metalloproteinases. Antivenom does not significantly prevent local tissue necrosis.

TCVD can simultaneously deliver multiple drugs that act synergistically to counteract, inhibit, neutralize and denature venom.

TCVD immediately reduces the pain at the site of the bite by the local anesthetic effects of dilute tumescent lidocaine.

The large volume of saline with TCVD can provide some supplemental fluids.

Significantly, dilution of a drug increases its solubility. Some drugs are considered incompatible because of precipitation when mixed together in the same solution. For example, mixing 1 gm of acyclovir (1 g/20 ml) with 1 gram of lidocaine (1 gram/100 ml) with epinephrine (1 mg/L) produces immediate precipitation within the 120 ml mixture. Dilution of 1 gm of acyclovir and 1 gm of lidocaine in 100 ml, 250 ml and 500 ml of saline also results in precipitation. However when 1 gm of acyclovir and 1 gm of lidocaine and 1 mg epinephrine are mixed in 1000 ml of saline, there is no precipitation. This tumescent solution can be safely and painlessly injected subcutaneously into a human patient. This is surprising and unexpected because the FDA approved package insert labeling for acyclovir for IV infusion states explicitly the subcutaneous delivery must be avoided. Similar increased solubility and drug-drug compatibility of mixtures of multiple contravenom drugs can be expected with sufficient tumescent dilution. This is a unique and unexpected advantage of tumescent contravenom delivery.

Subcutaneous Tumescent Drug Delivery Solutions

Subcutaneous tumescent drug delivery solutions may be defined as follows: 1) For any drug D that is commercially available as a liquid solution at a specified concentration C, a tumescent solution of drug D is any dilution of the drug that reduces the commercial concentration by a factor of 2 or more. Thus a tumescent solution of drug D has a concentration that is less than or equal to C/2. In other words a tumescent solution has been diluted at least 2-fold. The diluent can be any biocompatible fluid, for example water or a crystalloid solution such as Ringer's lactate or physiologic 0.9% sodium chloride.

2) If a drug is available as a lyophilized powder, and the FDA-approved reconstitution requires some specified minimal volume V of diluent, then any solution of D that is at least twice volume V is considered a tumescent solution of drug D.

Venoms

Numerous species produce venoms and harmful or lethal animal envenomation can be found worldwide (Zhang 2015 *Zoological Research* 36(4): 183-222). The methods of tumescent contravenom delivery disclosed here are useful in treating envenomation by venomous toxins produced by the following categories of venomous species.

Cnidarians

The toxicity of Cnidaria is a subject of concern for its influence on human activities and public health, as well as a potential source of natural bioactive compounds useful to develop new drugs or biomedical materials (Mariottini G L, Pane L Toxins (Basel). 2013 6(1):108-51).

Jellyfish

Jellyfish *Stomolophus meleagris* is one of the most dangerous jellyfish. People stung by the jellyfish suffer itch, edema, myalgia, dyspnea, hypotension, shock, and even death. The venom of *S. meleagris* contains various toxins including serine protease inhibitors, PLA2, potassium channel inhibitors, metalloproteases, C-type lectins, hemolysins, cytotoxins, cardiotoxins and neurotoxins. The identified toxins are probably related to the sting caused by the jellyfish (Li et al J Proteomics. 2014 Jun. 25; 106:17-29.).

Sea Anemone

Sea anemone toxins comprise mainly proteins and peptides, including different ion channel modulators, cytolysins, protease inhibitors and PLA2s, which are efficient in targeting different prey (Frazão et al, Mar Drugs. 2012 August; 10(8):1812-51). The neurotoxic fractions from the exudates of *Stichodactyla helianthus* and *Bunodosoma granulifera* were analyzed by reversed-phase chromatography and mass spectrometry. The resulting fractions were analyzed by their toxicity to crabs. The first peptide fingerprints of these sea anemones were assessed, revealing the largest number of peptide components (about 156 peptides) so far found in sea anemone species (Rodriguez et al, Peptides. 2012 March; 34(1):26-38).

*Hydra*

Like in other cnidarians, hydra polypeptide toxins are expressed mainly in nematocysts and represent a highly complex array of effector molecules aimed at paralyzing a prey and disintegrating its tissue (Rachamim & Sher, Int J Dev Biol. 2012; 56(6-8):605-11). The proteome of nematocysts from the freshwater polyp *Hydra magnipapillata* has been reported, which revealed an unexpectedly complex secretome of 410 proteins, from which 55 toxin-related sequences were found to be homologous with toxins in other venomous animals. These include neurotoxins, cytolysins, toxic phospholipases, many peptidases, and proteins of the SCP_GAPR-1-like family. The molecular masses of the toxins mainly range from 25 to 100×103 (Balasubramanian et al, J Biol Chem. 2012 287(13):9672-81). Small peptide toxins affecting ion channels identified in many sea anemones have not been determined in this analysis.

Molluscs (Cone Snails)

Cone snails (*Conus* species) are predatory molluscs that inhabit tropical and subtropical shallow seawater. The systematic mining of fish-hunting cone snail toxins began 30 years ago. Extensive studies revealed that their venom ducts produce a mixture of peptides, generally known as conotoxins, having exquisite specificity for different ion channels, receptors, and transporters (Olivera et al, Science. 1985 Dec. 20; 230(4732):1338-43; Olivera et al. Science. 1990 249(4966):257-63). They are mostly short disulfide-rich peptides of 10 to 40 amino acids with remarkable structural diversities. An emerging enigma concerning conotoxins is their striking diversity. It was estimated that each *Conus* species could produce more than 1 000 different conotoxins (Biass et al, J Proteomics. 2009 72(2):210-8; Davis et al, Peptides. 2009 30(7):1222-7). Conotoxin-encoding transcripts are diversified by hypermutation, fragment insertion/deletion, and mutation-induced premature termination, and a single mRNA species can produce multiple toxin products through alternative post-translational modifications and alternative cleavages of the translated precursor (Lu et al, Mol Cell Proteomics. 2014 13(1):105-18).

Annelids (Leeches)

Leeches are hematophagous annelids. They penetrate the body surface of the host and have to take measures to inhibit the normal reactions in host tissues to blood vessel damage, including blood coagulation, swelling, pain and inflammation. Long term evolution made leeches have acquired the ability to control these processes in their hosts by transferring various bioactive substances to the host through tiny salivary ductile (Baskova et al, Biochemistry (Mosc). 2008 March; 73(3):315-20; Lemke et al, PLoS One. 2013 8(9): e73809). An expressed sequence tag (EST) library-based analysis of the salivary transcriptome of the North American medicinal leech (*Macrobdella decora*) revealed a complex cocktail of anticoagulants and other bioactive secreted proteins, including saratin, bdellin, destabilase, hirudin, decorsin, endoglucoronidase, antistatin, and eglin, as well as to other previously uncharacterized serine protease inhibitors, lectoxin-like c-type lectins, ficolin, disintegrins and histidine-rich proteins (Min et al, J Parasitol. 2010 96(6): 1211-21).

Arthropods

Spiders

Spiders (order Araneae) are the most successful venomous animals in term of their species and toxin diversification, and spider venoms have been intensively investigated. The major components of most spider venoms are small disulfide-bridged peptides, and more than 1 000 spider toxins have been characterized from about 90 species (Herzig et al, Nucleic Acids Res. 2011 39 (Database issue):D653-7). From Chinese bird spider (*Ornithoctonus huwena*), 626 toxin precursor sequences in total were retrieved from the transcriptomic data and were clustered into 16 gene superfamilies, including six novel superfamilies and six novel cysteine patterns (Zhang et al, PLoS One. 2014 9(6):e100682). Many spider toxins described to date contain an unusual structural motif known as a cystine knot, which is typically highly resistant to proteases, acidic pH, high temperatures and organic solvents (Saez et al, Toxins (Basel). 2010 2(12): 2851-71). Spider toxins mainly target various ion channels and exhibit a range of pharmacological activities, including Ca2+, K+, Na+ channels, transient receptor potential (TRP) channels, mechanosensitive channels, acid-sensing ion channels (ASICs), glutamate receptors and glutamate transporters (King & Hardy, Annu Rev Entomol. 2013; 58:475-96).

Scorpions

Though scorpions are a small arachnid group, they constitute a very well adapted order of predatory animals that have been living in the Earth for nearly 400 million years (Polis, 1990. The Biology of Scorpions. California, Palo Alto: Stanford University Press). Individual scorpion venoms often contain as many as several hundred components (Almeida et al, BMC Genomics. 2012 13:362; Xu et al, J Proteomics. 2014 106:162-80), and by coupling with measures of taxonomic diversities of scorpions, this has led to estimates of ~100,000 bioactive peptides in the venoms of scorpions (King, Expert Opin Biol Ther. 2011 11(11):1469-84). Scorpion cysteine-stabilised α/β (CSα/β) toxins are disulfide-bridged peptides with a significantly constrained structure, possess pharmacological action on ion channels, including Ca2+, Na+, K+, Cl— channels (Ortiz et al, Toxicon. 2015 93:125-35). Non-disulfide-bridged peptides constitute an important group of scorpion venom components. The pharmacological properties of these linear peptides include antimicrobial, cytolytic, antiviral, antimalarial, bradykinin potentiating and immuno-modulating activities (Al-maaytah & Albalas, Peptides. 2014 51:35-45). Interestingly, it has been shown that a majority of CSα/β toxin scaffolds have experienced episodic influence of positive selection, while most non-CSα/β linear toxins evolve under the extreme influence of negative selections (Sunagar et al, Toxins (Basel). 2013 5(12):2456-87).

Centipedes

Centipedes are excellent predatory arthropods. Recently, centipede *Scolopendra subspinipes dehaani* venom was systematically investigated by transcriptomic and proteomic analysis coupled with biological function assays. In total, 543 venom proteins and peptides were cloned, and 50 proteins/peptides were purified from the venom (Liu et al, J Proteome Res. 2012 11(12):6197-212). In another report, 26 neurotoxin-like peptides belonging to 10 groups were identified from the venom of *Scolopendra subspinipes mutilans* (Yang et al, Mol Cell Proteomics. 2012 11(9):640-50). The purified toxins mainly possessed various ion channel modulating properties. Most of them showed no significant sequence similarity to other proteins and peptides deposited in the known public database. These works provide a novel reservoir of mining ion channel modulating agents. Furthermore, a selective NaV1.7 inhibitor (named μ-SLPTX-Ssm6a) with analgesic efficacy as assayed in rodent pain models was discovered, which might be a promising lead molecule for the development of novel analgesics targeting NaV1.7 (Yang et al, Proc Natl Acad Sci USA. 2013 110 (43):17534-9).

Bees and Wasps

An in-depth study of honeybee (*Apis mellifera*) venom proteome revealed an unexpectedly rich venom composition, in which in total of 102 proteins and peptides were found. A group of 33 putative toxins is proposed to contribute to venom activity by exerting toxic functions or by playing a role in social community (Van Vaerenbergh et al, Subcell Biochem. 2014; 80:3-6). There are two major forms of honeybee venom used in pharmacological applications: manually extracted glandular venom, and venom extracted through the use of electrical stimulation. A proteome comparison data demonstrated that these two venom forms are different in their compositions, which are important in their use as pharmacological agents (Li et al, BMC Genomics. 2013 14:766). An optimized experimental protocol was used for the detection of peptides in the venom of the social wasp *Polybia paulista*. The results revealed a surprisingly high level of intra- and inter-colonial variability for the same wasp species, which detected 78-108 different peptides in the venom of different colonies of *P. paulista* with molecular mass range from 400 to 3 000×103; among those, only 36 and 44 common peptides were observed in the inter- and intra-colony comparisons, respectively (Dias et al, Peptides. 2014 51:122-30).

Ants

Ants (*Hymenoptera, Formicidae*) represent a taxonomically diverse group of arthropods comprising more than 10,000 species. Ant venom components exhibit a variety of biological activities, including antimicrobial, haemolytic, cytolytic, paralytic, insecticidal and pain-producing activities (Aili et al, Toxicon. 2014 92:166-78). Transcriptomic analysis for Brazilian ant (*Tetramorium bicarinatum*) venom revealed a high diversification of the venom components, including venom allergens, distinct isoforms of PLA1 and PLA2, serine proteases, hyaluronidases, protease inhibitors, secapin, waprin-like and agatoxins (Bouzid et al, BMC Genomics. 2014 15:987). About 40% of the generated sequences have no hits in the databases, emphasizing the existence of many new unknown molecules. From the venom gland of the predatory giant ant *Dinoponera quadriceps*, inhibitor cysteine-knot (ICK)-like toxins, insect allergens, enzymes, and lethal toxins were determined (Torres et al, PLoS One. 2014 9(1):e87556). Ant venoms, similar to those of bees and wasps, contain many allergens, which are the most frequent elicitors of anaphylaxis in humans.

Sharing some common toxins in venoms, each species of ants appears to have a number of unique components. Interestingly, the nesting habits of ants have deeply influenced their venom toxicity and composition. In ant genus *Pseudomyrmex*, the venom of the ground-dwelling species, *Pseudomyrmex termitarius* is composed of 87 linear peptides. However, the venoms of the arboreal and the plant-ant species, *P. penetrator* and *P. gracilis*, contain 26 and 23 peptides with disulfide bonds, respectively (Touchard et al, Toxicon. 2014 88:67-76). The large number of peptides in *P. termitarius* venom is likely related to potential prey diversity plus the antibacterial peptides required for nesting in the ground.

Ticks and Horseflies

As haematophagous arthropods and for biological success, ticks use their salivary constituents to successfully obtain a blood meal by targeting major physiological pathways involved in host defense mechanisms. The resulting feeding site also becomes a favorable environment for many pathogens to exploiting ticks to facilitate their transmission to the host (Wikel, Front Microbiol. 201 4:337). It has been reported that tick salivary gland extract inhibits host complement activation and depresses macrophage function by inhibiting lipopolysaccharide (LPS)-induced nitric-oxide synthesis and proinflammatory cytokine production (Cabezas-Cruz & Valdés, Front Zool. 2014 11:47; Stibrániová et al, Acta Virol. 2013 57(2):200-16).

In traditional Eastern medicine, horseflies are used as anti-thrombosis material for hundreds of years. Similar to other hematophagous arthropods, such as mosquitoes (Arcá et al, Proc Natl Acad Sci USA. 1999 96(4):1516-21), several families of proteins or peptides, which act mainly on the hemostatic system or immune system of the host, were identified in the horsefly *Tabanus yao* salivary glands. These include fibrinogenolytic enzymes, RGD-containing anti-platelet aggregation disintegrins, thrombin inhibitors, vasodilator peptides, peroxidase and apyrase (Ma et al, Mol Cell Proteomics. 2009 8(9):2071-9; Xu et al, Mol Cell Proteomics. 2008 7(3):582-90). The diversity of anti-thrombosis components in horsefly saliva reflects the molecular basis of its blood-sucking living strategy.

Echinoderms

Starfishes and Sea Urchins

Starfishes and sea urchins are the popular name for marine invertebrates that belong to the phylum Echinodermata. Comparatively speaking, studies on their venoms are still in a primitive stage. Some species of starfishes and sea urchins are dangerous to humans. When stung by the venomous spines on the surface of crown-of-thorns starfish (*Acanthaster planci*), various pathological symptoms, such as severe pain, redness, swelling, and protracted vomiting, are induced (Sato et al, J Dermatol. 2008 35(3):162-7). The crude venom extracted from the spines exhibits diverse biological effects, including hemolytic, mouse lethal, edema-forming, PLA2, anticoagulant and cytotoxic activities (Butzke & Luch, E X S. 2010; 100:213-32; Lee et al, Toxicon. 2014 91:126-34). In the case of sea urchins, envenomations are caused by stings from either pedicellariae or spines (Balhara & Stolbach, Emerg Med Clin North Am. 2014 32(1):223-43). A galactose-binding lectin SUL-I was isolated from the venom of sea urchin *Toxopneustes pileolus*, which showed mitogenic, chemotactic, and cytotoxic activities through binding to carbohydrate chains on cells (Hatakeyama et al, Toxicon. 2015 94:8-15). Cathepsin B/X was found to be secreted by *Echinometra lucunter* sea urchin spines, a structure rich in granular cells and toxins, which was thought to participate in the inflammatory response to the accident (Sciani et al, J Venom Anim Toxins Incl Trop Dis. 2013 19(1):33).

Venomous Vertebrates

Fishes

Despite the large number of species, compared with other groups of venomous organisms, the study on fish venoms is still in a relatively preliminary state and fish venoms are neglected source of bioactive proteins and peptides. Protein toxins natterins were characterized from Brazilian venomous fish *Thalassophryne nattereri* (Magalhães et al, Biochimie. 2005 87(8):687-99). Natterins and their analogues might be widely distributed in the fish venom glands, thereby forming one family of fish venom toxins (Tamura et al, Toxicon. 2011 58(5):430-8). The difficulty in the study of fish venoms is that the venoms are sensitive to heat, pH, and lyophilization, as well as are often contaminated with mucus components. A novel protein-handling protocol has been developed recently, upon which the investigation of fish venom composition using barb tissue from the blue-spotted stingray (*Neotrygon kuhlii*) was carried out. The results revealed a variety of protein types that are novel to animal toxins. Putative venom toxins identified include cystatin, peroxiredoxin and galectin (Baumann et al, J Proteomics. 2014 109:188-98).

Amphibians

Amphibians might not be considered as typical venomous animals due to the lack of a venom delivery system. Amphibian skin is naked to fulfill special physiological requirements, such as respiration and water-salt balance (Campbell et al, Int J Biochem Cell Biol. 2012 44(3):431-4; Duellman & Trueb, 1994. Relationship with the environment. In: Duellman W E, Trueb L. Biology of Amphibians. Maryland: The Johns Hopkins University Press, 197-228). Thus, the skin has to form a special defense system to withstand constantly confronted injurious mechanical, chemical and biological factors. Defensive (innate immunity) responses against potential invading of pathogens and repairing capacity of the disrupted surface layer of cells are essential (Voyles et al, Science. 2009 326(5952):582-5). Amphibian skin contains an arsenal of bioactive molecules to fulfill the related functions (Konig et al, Peptides. 2015 63:96-117; Zhang, Zoological Research, 27(1): 101-112). Indeed, there are many poisonous frogs, including *Dendrobatidae, Mantellidae, Bufonidae,* and *Myobatrachidae,* which are very "toxic" to mammals and caused by alkaloids sequestered from dietary alkaloid-containing arthropods (Daly et al, J Nat Prod. 2005 68(10):1556-75; Hantak et al, J Chem Ecol. 2013 39(11-12):1400-6). The toxicity of some amphibian species to mammals results from physiological proteins and peptides secreted in the skin mucus (Lai et al, Zoological Research, 23(2): 113-119; Lai et al., Peptides. 2002 23(3):427-35; Liu et al, PLoS One. 2008 3(3):e1770; Qian et al, Toxicon. 2008 July; 52(1):22-31; Qian et al. Toxicon. 2008 52(2):285-92). Many amphibian skin peptides are related to mammalian hormones or neurotransmitters, as well as antimicrobial peptides (Xu & Lai, Chem Rev. 2015 Feb. 25; 115(4):1760-846; Zhang, Zoological Research, 27(1): 101-112).

Several hundreds of peptides were identified from Chinese odorous frogs (Li et al, Mol Cell Proteomics. 2007 6(5):882-94; Yang et al, J Proteome Res. 2012 Jan. 1; 11(1):306-19). The function of frog skin peptides are diverse, including antimicrobial, antioxidant, immunomodulatory, and metabolic regulatory activities (Conlon et al, Peptides. 2014 57:67-77; Yang et al, J Proteome Res. 2012 11(1):306-19). Under environmental pressure, gene duplication, rapid mutation at the amino acid level, domain shuffling and conversion are among the major forces in the formation of heavy diversification of peptides in frog skin (Duda et al, Mol Biol Evol. 2002 19(6):858-64; Lee et al, Eur J Immunol. 2005 35(4):1220-9; Roelants et al, PLoS Genet. 2013; 9(8):e1003662). This evolution pattern is very similar to those of toxins in venomous animals.

Snakes

Snake venoms comprise a diverse array of toxins that have a variety of pharmacological and toxicological effects, and are conveniently classified as hemotoxic and neurotoxic (Du, Blood Cells Mol Dis. 2006 36(3):414-21; Kini, J Thromb Haemost. 2011 9 Suppl 1:195-208; Kularatne & Senanayake, Handb Clin Neurol. 2014; 120:987-1001). Most of the snake toxins were recruited or derived from the normal body proteins in the common ancestor of venomous squamates (Toxicofera) or advanced snakes (Caenophidia) during 100-200 MYA (Fry, Genome Res. 2005 15(3):403-20; Fry et al, Annu Rev Genomics Hum Genet. 2009; 10:483-511; Fry et al. Mol Cell Proteomics. 2010 9(11): 2369-90). By using cutting-edge proteomic and transcriptomic approaches, the venomics of various venomous snake species have been conducted (Brahma et al, Toxicon. 2015 93:1-10; Calvete, Expert Rev Proteomics. 2014 11(3):315-29).

The toxin profiles of elapid snakes *Naja naja* and *Bungarus multicinctus* were analyzed by sequencing their venom gland transcriptomes (Jiang et al, BMC Genomics. 2011 12:1). Totally 1,092 valid expressed sequences tags (ESTs) for *B. multicinctus* and 1,172 ESTs for *N. atra* were generated. The major components of *B. multicinctus* venom are neurotoxins, including long chain alpha-neurotoxins and recently originated beta-bungarotoxin, whereas, *N. atra* venom mainly contains 3FTs with cytotoxicity and neurotoxicity (short chain alpha-neurotoxins). A recent expansion of alpha-neurotoxins genes in *N. atra* was observed. Tandem duplications contributed the most to the expansion of toxin multigene families. Furthermore, not only the multigene toxin families but also the less abundant toxins were under rapid adaptive evolution (Jiang et al, BMC Genomics. 2011 12:1).

Lizards

The lizards of genus *Heloderma*, which live in the southwestern part of the North American continent, have been recognized as venomous for more than a century. Envenomations of humans by helodermatid lizards may cause complicated symptoms including extreme pain, acute local swelling, nausea, fever, hypotension, and inhibition of blood coagulation (Koludarov et al, Toxins (Basel). 2014 6(12): 3582-95). Lizard venoms contain a cocktail of different proteins and peptides including hyaluronidase, PLA2s, kallikrein-like proteases, helokinestatin, helofensin, as well as bioactive peptides including hormone-like exendin peptides (Fry et al, Mol Biol Evol. 2010 27(2):395-407; Mol Cell Proteomics. 2010 9(11):2369-90). In a recent study attempting to characterize the gila monster (*Heloderma suspectum suspectum*) venom proteome, a total of 39 different proteins were identified out of the 58 selected spots that represent the major constituents of the venom. A neuroendocrine convertase 1 homolog was identified, which is likely to converts the proforms of exendins into the mature and active forms (Sanggaard et al, J Proteomics. 2015 117:1-11).

Venomous Mammals

The northern short-tailed shrew (*Blarina brevicauda*) saliva contains *blarina* toxin (Kita et al, Proc Natl Acad Sci USA. 2004 101(20):7542-7) showing kallikrein-like protease activity. This toxin cleaves kininogens to release kinins, including bradykinin, which are inflammation mediators. *Blarina* toxin shows sequence homologous to gila toxin and horridum toxin, two toxins from the Mexican beaded lizard. *Blarina* toxin and gila toxin have served as nice molecular models to study the structural basis of transition from a non-toxic to a toxic kallikrein, which is also a good example of convergent evolution at the molecular level (Aminetzach et al, Curr Biol. 2009 19(22):1925-31). Two distinct classes of anticoagulants are found in the saliva of vampire bats, i.e., plasminogen activators and inhibitors of proteinases (Ligabue-Braun et al, Toxicon. 2012 59(7-8):680-95).

The platypus venom contains natriuretic peptides, defensin-like peptides, nerve growth factors, isomerases, hyaluronidase, proteases, mammalian stress response proteins, cytokines, and other immune molecules (Wong et al, Mol Cell Proteomics. 2012 11(11):1354-64). Gene duplication and subsequent functional diversification of beta-defensins gave rise to platypus *Ornithorhynchus* venom defensin-like peptides (Whittington et al, Genome Res. 2008 18(6):986-94). The brachial gland exudates of primate slow lorises contain a new member of the secretoglobin family, which is a 17.6×103 heterodimeric protein homologous to Fel 1d, the major allergen from domestic cat (Nekaris et al, J Venom Anim Toxins Incl Trop Dis. 2013 19(1):21). This is in accordance with the variable sensitivity to loris bites and the onset of anaphylaxis caused.

EXAMPLE 1

Treatment of an Envenomation by Administration of Tumescent Contravenom Solution A subject presenting with a snake bite from a saw-scaled viper (*Echis carinatus*) is treated with tumescent contravenom delivery. 2.28 μg Varespladib (LY315920), molecular weight 380.39 g/mole; 300 mg lidocaine; 0.3 mg epinephrine; and 3 meq sodium bicarbonate are dissolved in a saline solution to a total volume of 280 ml, resulting in a concentration of 24.8 nM Varespladib, i.e., 4× the IC50 value of 6.2 nM. The solution is then infiltrated in the area of the envenomation using a blunt tipped infiltration cannula (i.e., sprinkler-tip or Klein™ needle infiltrators). The tumescent contravenom delivery treatment retards the systemic absorption of venom and inactivates harmful venom constituents, thereby preventing life-threatening complications. The tumescent contravenom delivery is performed by the victim himself/herself and/or by another person.

The subject is examined for 12-24 hours after infiltration, preferably including a professional evaluation at a medical facility for snake venom symptoms including swelling and redness around the wounds, pain at the bite site, difficulty breathing, vomiting and nausea, blurred vision, sweating and salivating and numbness in the face and limbs.

EXAMPLE 2

Tumescent ContraVenom for Treating Scorpion Envenomation

Incidence of Scorpion Envenomation

In many parts of the world, scorpion stings and envenomations are a significant public health problem. It is estimated that the incidence of scorpion envenomation is more than 1 million cases per year. Severe complications occur more frequent in children with a mortality rate of up to 9%. (Miranda C H et al. 2015 *Am J Emerg Med* 33:862). (Guidine P A et al. 2014 *Toxicol Sci* 137:147-57).

Among American troops in Saudi Arabia the estimated incidence of scorpion sting was 24 per 1000 troops. (Groshong T D 1993 *Ann Emerg Med* 22:1431-7).

Mexico has the highest diversity of scorpions in the world, having 281 different species. (Isbister G K et al. 2014 *N Engl J Med* 371:457-63).

Clinical Presentation

The physical presentation of a scorpion envenomation includes cold extremities, sweating, and an obtunded level of consciousness. Manifestations of scorpion envenomations include hyper-intense painful local reactions. Cases of severe envenomation involve potentially fatal cardiogenic shock, pulmonary edema, respiratory failure, and neurological toxicity.

Severe scorpion envenomation affects 2% of cases. Risk factors for severe scorpion envenomation include size of patient, sting on torso, head or neck, and length of time between sting and medical care.

Pathophysiology of Scorpion Venom

The neurotoxins in scorpion venom are potent activators of the autonomic nervous system leading to massive catecholamine release, precipitating intense vasoconstriction that eventuates in toxic myocarditis, adrenergic myocarditis, and ischemic myocarditis, with cardiac insufficiency leading pulmonary edema and life threatening hypotension.

Current Treatment of Scorpion Envenomation

Antivenin, vasodilators, and benzodiazepines are medications of choice in the treatment of scorpion bites. Anaphylaxis to antivenin is possible but may be difficult to diagnose because of the effects of scorpion venom. (Bhoite R R et al. 2015 *Indian J Crit Care Med* 19:547-9).

Scorpion antivenom (SAV) is most effective if given in less than 2 hours after envenomation. (Ben Othman A et al. 2016 *Tunis Med* 94:102-6).

Prazosin is a sympatholytic vasodilator, used for treating hypertension, which counteracts the vasoconstrictive effects of excessive endogenous catecholamine. Prazosin is an al-blocker which acts on alpha-1 adrenergic receptors on vascular smooth muscle to block the vasoconstrictive action of norepinephrine. (Pandi K et al. 2014 *Arch Dis Child* 99:575-80).

Supportive and symptomatic treatment for severe scorpion envenomation includes intubation, analgesics, and dobutamine to treat hypotension.

TLA for Scorpion Sting

The pain of a scorpion sting is immediate, increases over 1 to 2 hours, becomes overwhelmingly intense and lasts for days, then decreases over weeks. Based on the immediate alleviation of acute Herpes zoster pain by tumescent lidocaine anesthesia (TLA) that we have observed, the immediate local anesthesia provided TLA will also eliminate the pain of a scorpion sting. Furthermore, TLA may reduce the rate of systemic absorption of scorpion venom and thereby prolong the window of time between the scorpion sting and an SAV injection wherein SAV is effective. (Donat N et al. 2011 *Mil Med* 176:472-4).

H4 histamine receptor, expressed in white blood cells, regulates neutrophil release from bone marrow and mediates eosinophil shape change and mast cell chemotaxis. In a mouse model of scorpion envenomation, pretreatment with H1, H2, or H4 type antihistamines markedly alleviated inflammation in heart and lungs induced by scorpion toxin. (Lamraoui A et al. 2014 *Inflammation* 37:1689-704).

Tumescent ContraVenom (TCV) Treatment for Scorpion Envenomation

TCV treatment is advantageous as a pre-hospital first aid treatment of scorpion envenomation. A TCV solution for scorpion envenomation consists of a variety of compatible medications, which counteract scorpion venom, dissolved in a solution of tumescent lidocaine anesthesia (TLA).

TLA contains dilute epinephrine producing widespread localized vasoconstriction. TLA vasoconstriction, by delaying the systemic absorption of venom, prolongs the time interval between scorpion envenomation and presentation for medical care in a hospital setting.

TLA immediately relieves the pain of scorpion sting. TLA is safe in children. TLA is easily injected by persons with minimal first aid training.

A TCV solution contains a variety of drugs having an additive or synergistic effect on counteracting scorpion venom. For example, prazosin and H4-type antihistamine in a TCV solution are effective treating scorpion envenomation.

EXAMPLE 3

Estimated Maximal Safe Dosages of Tumescent Lidocaine

Background:

Tumescent lidocaine anesthesia consists of subcutaneous injection of relatively large volumes (up to 4 L or more) of dilute lidocaine (≤1 g/L) and epinephrine (≤1 mg/L). Although tumescent lidocaine anesthesia is used for an increasing variety of surgical procedures, the maximum safe dosage is unknown. Our primary aim in this study was to measure serum lidocaine concentrations after subcutaneous administration of tumescent lidocaine with and without liposuction. Our hypotheses were that even with large doses (i.e., >30 mg/kg), serum lidocaine concentrations would be below levels associated with mild toxicity and that the concentration-time profile would be lower after liposuction than without liposuction.

Methods:

Volunteers participated in 1 to 2 infiltration studies without liposuction and then one study with tumescent liposuction totally by local anesthesia. Serum lidocaine concentrations were measured at 0, 2, 4, 6, 8, 10, 12, 14, 16, 18, and 24 hours after each tumescent lidocaine infiltration. Area under the curve (AUC∞) of the serum lidocaine concentration-time profiles and peak serum lidocaine concentrations (Cmax) were determined with and without liposuction. For any given milligram per kilogram dosage, the probability that Cmax >6 μg/mL, the threshold for mild lidocaine toxicity was estimated using tolerance interval analysis.

Results:

In 41 tumescent infiltration procedures among 14 volunteer subjects, tumescent lidocaine dosages ranged from 19.2 to 52 mg/kg. Measured serum lidocaine concentrations were all <6 μg/mL over the 24-hour study period. AUC∞s with liposuction were significantly less than those without liposuction (P=0.001). The estimated risk of lidocaine toxicity without liposuction at a dose of 28 mg/kg and with liposuction at a dose of 45 mg/kg was ≤1 per 2000.

Conclusions:

Preliminary estimates for maximum safe dosages of tumescent lidocaine are 28 mg/kg without liposuction and 45 mg/kg with liposuction. As a result of delayed systemic absorption, these dosages yield serum lidocaine concentrations below levels associated with mild toxicity and are a nonsignificant risk of harm to patients.

Tumescent lidocaine anesthesia (TLA) was developed for performing liposuction totally by local anesthesia with virtually no surgical blood loss (Klein J A. The tumescent technique for liposuction surgery. J Am Acad Cosmetic Surg 1987; 4:263-7; and Klein J A. Tumescent technique for local anesthesia improves safety in large-volume liposuction. Plast Reconstr Surg 1993; 92:1085-98). TLA has been extended to a wide range of other surgical procedures involving cutaneous, subcutaneous, breast, and vascular tissues (Shimizu Y, Nagasao T, Taneda H, Sakamoto Y, Asou T, Imanishi N, Kishi K. Combined usage of intercostal nerve block and tumescent anaesthesia: an effective anaesthesia technique for breast augmentation. J Plast Surg Hand Surg 2014; 48:51-5; Sleth J C, Servais R, Saizy C. "Tumescent infiltrative anaesthesia for mastectomy: about six cases" Ann Fr Anesth Reanim 2008; 27:941-4; Orgill D P. Excision and skin grafting of thermal burns. N Engl J Med 2009; 360: 893-901; Bussolin L, Busoni P, Giorgi L, Crescioli M, Messeri A. Tumescent local anesthesia for the surgical treatment of burns and postburn sequelae in pediatric patients. Anesthesiology 2003; 99:1371-5; Gümüş N. Tumescent infiltration of lidocaine and adrenaline for burn surgery. Ann Burns Fire Disasters 2011; 24:144—Blome-Eberwein S, Abboud M, Lozano D D, Sharma R, Eid S, Gogal C. Effect of subcutaneous epinephrine/saline/local anesthetic versus saline-only injection on split-thickness skin graft donor site perfusion, healing, and pain. J Burn Care Res 2013; 34:e80-6; Cohn M S, Seiger E, Goldman S. Ambulatory phlebectomy using the tumescent technique for local anesthesia. Dermatol Surg 1995; 21:315-8; Vuylsteke M E, Mordon S R. Endovenous laser ablation: a review of mechanisms of action. Ann Vasc Surg 2012; 26:424-33; Barkmeier L D, Hood D B, Sumner D S, Mansour M A, Hodgson K J, Mattos M A, Ramsey D. Local anesthesia for infrainguinal arterial reconstruction. Am J Surg 1997; 174: 202-4; Bush R G, Hammond K A. Tumescent anesthetic technique for long saphenous stripping. J Am Coll Surg 1999; 189:626-8; Haines W Y, Deets R, Lu N, Matsuura J H. Tumescent anesthesia reduces pain associated with balloon angioplasty of hemodialysis fistulas. J Vasc Surg 2012; 56:1453-6; Behroozan D S, Goldberg L H. Dermal tumescent local anesthesia in cutaneous surgery. J Am Acad Dermatol 2005; 53:828-30; Girard C, Debu A, Bessis D, Blatière V, Dereure O, Guillot B. Treatment of Gorlin syndrome (nevoid basal cell carcinoma syndrome) with methylaminolevulinate photodynamic therapy in seven patients, including two children: interest of tumescent anesthesia for pain control in children. J Eur Acad Dermatol Venereol 2013; 27:e171-5; Kendler M, Micheluzzi M, Wetzig T, Simon J C. Electrochemotherapy under tumescent local anesthesia for treatment of cutaneous metastases. Dermatolog Surg. 2013; 39:1023-32; Stoffels I, Dissemond J, Schulz A, Hillen U, Schadendorf D, Klode J. Reliability and cost-effectiveness of complete lymph node dissection under tumescent local anaesthesia vs. general anaesthesia: a retrospective analysis in patients with malignant melanoma AJCC stage III. J Eur Acad Dermatol Venereol 2012; 26:200-6; Ramon Y, Barak Y, Ullmann Y, Hoffer E, Yarhi D, Bentur Y. Pharmacokinetics of high-dose diluted lidocaine in local anesthesia for facelift procedures. Ther Drug Monit 2007; 29:644-7; Abramson D L. Tumescent abdominoplasty: an ambulatory office procedure. Aesthetic Plast Surg 1998; 22:404-7; Narita M, Sakano S, Okamoto S, Uemoto S, Yamamoto M. Tumescent local anesthesia in inguinal herniorrhaphy with a PROLENE hernia system: original technique and results. Am J Surg 2009; 198:e27-31; Kayaalp C, Olmez A, Aydin C, Piskin T. Tumescent local anesthesia for excision and flap procedures in treatment of pilonidal disease. Dis Colon Rectum 2009; 52:1780-3; Locke M, Windsor J, Dunbar P R. Human adipose-derived stem cells: isolation, characterization and applications in surgery. ANZ J Surg 2009; 79:235-44; Prasetyono T O. Tourniquet-Free Hand Surgery Using the One-per-Mil Tumescent Technique. Arch Plast Surg 2013; 40:129-33; Mizukami T, Hamamoto M. Tumescent local anesthesia for a revascularization of a coronary subclavian steal syndrome. Ann Thorac Cardiovasc Surg 2007; 13:352-4; and Carlson G W. Total mastectomy under local anesthesia: the tumescent technique. Breast J 2005; 11:100-2). The maximum safe dosage of tumescent lidocaine for these procedures is unknown. There is a need for a pharmacokinetic-based estimate of the maximum safe milligram per kilogram dosage of tumescent lidocaine (Rosenberg P H, Veering B T, Urmey W F. Maximum recommended doses of local anesthetics: a multifactorial concept. Reg Anesth Pain Med 2004; 29:564-75; and Scott D B. "Maximum recommended doses" of local anaesthetic drugs. Br J Anaesth 1989; 63:373-4). The package insert labeling approved by the United States Food and Drug Administration (FDA) for lidocaine with epinephrine states that the recommended maximal dosage is 7 mg/kg for infiltration local anesthesia. The FDA has no data to support this 7 mg/kg as the dosage limit, which was established in 1948 for epidural anesthesia. The liposuction guidelines of the American Society for Dermatologic Surgery recommended that the maximal safe milligram per kilogram dosage of tumescent lidocaine for liposuction totally by local anesthesia is 55 mg/kg (Coldiron B, Coleman III W P, Cox S E, Jacob C, Lawrence N, Kaminer M, Narins R S. ASDS guidelines of care for tumescent liposuction. Dermatol Surg 206; 32:709-16).

Tumescent lidocaine solution contains at most 1 g lidocaine and 1 mg epinephrine in 100 mL plus 10 mEq sodium bicarbonate in 10 mL added to 1000 mL of 0.9% physiologic saline for a final lidocaine concentration of 1 g per bag containing 1110 mL or 0.9 g/L (0.09%). Sodium bicarbonate reduces the stinging discomfort of large volume subcutaneous tumescent infiltration (McKay W, Morris R, Mushlin P. Sodium bicarbonate attenuates pain on skin infiltration with lidocaine, with or without epinephrine. Anesth Analg 1987; 66:572-4).

Subcutaneous infiltration of large volumes of TLA solution causes the targeted tissue to become temporarily swollen and firm or tumescent. The resulting increased subcutaneous interstitial pressure spreads the TLA solution through adjacent tissues by bulk flow. Lidocaine toxicity is a function of serum lidocaine concentration. Dilute epinephrine produces intense local vasoconstriction, slows systemic absorption of lidocaine, and thus reduces peak serum lidocaine concentrations, which reduces the risk of systemic lidocaine toxicity. The removal of a significant volume of tumescent subcutaneous fat by liposuction removes a significant portion of the tumescent lidocaine before it is absorbed into the systemic circulation. The threshold serum concentration for mild lidocaine toxicity (lightheadedness, paresthesias, tinnitus, blurred vision, nystagmus, ataxia, slurred speech, confusion) is 6 μg/mL (Gianelly R, von der Groeben J O, Spivack A P, Harrison D C. Effect of lidocaine on ventricular arrhythmias in patients with coronary heart disease. N Engl J Med 1967; 277:1215-9; Scott D B. Evaluation of the toxicity of local anaesthetic agents in man. Br J Anaesth 1975; 47:56-61; and Rosaeg O P, Bell M, Cicutti N J, Dennehy K C, Lui A C, Krepski B. Pre-incision infiltration with lidocaine reduces pain and opioid consumption after reduction mammoplasty. Reg Anesth Pain Med 1998; 23:575-9).

The principal aim of our research was to measure serum lidocaine concentrations as a function of milligram per kilogram dosage of tumescent lidocaine. Our main hypothesis was that dosages of tumescent lidocaine that are considerably larger than 7 mg/kg are a nonsignificant risk of harm to patients.

The research had 4 specific aims. The first specific aim was to measure sequential serum lidocaine concentrations over 24 hours for each subject after subcutaneous infiltration of TLA on 3 separate occasions where the initial infiltrations were followed by no liposuction and the last infiltration was followed by liposuction. It has been suggested that IV lidocaine may have beneficial perioperative effects (Garutti I, Rancan L, Simon C, Cusati G, Sanchez-Pedrosa G, Moraga F, Olmedilla L, Lopez-Gil M T, Vara E. Intravenous lidocaine decreases tumor necrosis factor alpha expression both locally and systemically in pigs undergoing lung resection surgery. Anesth Analg 2014; 119:815-28; De Oliveira G S Jr, Fitzgerald P, Streicher L F, Marcus R J, McCarthy R J. Systemic lidocaine to improve postoperative quality of recovery after ambulatory laparoscopic surgery. Anesth Analg 2012; 115:262-7; Yon J H, Choi G J, Kang H, Park J M, Yang H S. Intraoperative systemic lidocaine for preemptive analgesics in subtotal gastrectomy: a prospective, randomized, double-blind, placebocontrolled study. Can J Surg 2014; 57:175-82; Kim K T, Cho D C, Sung J K, Kim Y B, Kang H, Song K S, Choi G J. Intraoperative systemic infusion of lidocaine reduces postoperative pain after lumbar surgery: a double-blinded, randomized, placebo-controlled clinical trial. Spine J 2014; 14:1559-66; and Grigoras A, Lee P, Sattar F, Shorten G. Perioperative intravenous lidocaine decreases the incidence of persistent pain after breast surgery. Clin J Pain 2012; 28:567-72). We hypothesized that tumescent infiltration without liposuction produces a serum lidocaine concentration-time profile resembling a constant IV infusion lasting 12 to 16 hours or more. Furthermore, we hypothesized that liposuction removes significant amounts of lidocaine before it can be systemically absorbed. If the later hypothesis is true, then lidocaine data derived from liposuction patients cannot be used to establish the maximum recommended milligram per kilogram dosage of tumescent lidocaine for surgical procedures that do not involve liposuction.

The second aim was to record heart rate associated with doses of tumescent epinephrine and document adverse signs or symptoms associated with serum lidocaine concentrations. We hypothesized that tachycardia is uncommon and that adverse events associated with the large dosages of tumescent lidocaine and epinephrine are uncommon.

The third aim was to analyze the association between the milligram per kilogram dosage of tumescent lidocaine and subsequent peak serum lidocaine concentrations (Cmax) both without and with liposuction. We hypothesized that there is a linear relationship between the milligram per kilogram dosage of tumescent lidocaine and Cmax. Such a linear relationship would allow one to estimate Cmax as a function of milligram per kilogram dosage of tumescent lidocaine.

The fourth aim was to use tolerance interval analysis to calculate the proportion of individuals who, when given a specified milligram per kilogram dosage of tumescent lidocaine, will have a Cmax exceeding 6 μg/mL. We hypothesized that there are dosages larger than 7 mg/kg that are associated with a risk of mild lidocaine toxicity (Cmax ≥6 μg/mL) of <1/1000 and therefore are a nonsignificant risk of harm to patients.

Methods

This research was supported by the authors and registered at clinicaltrials.gov: NCT00977028. Before every procedure, subjects signed written informed consent approved by an IRB.

Inclusion criteria were ASA physical status I or II, no use of drugs that inhibit platelet function or inhibit the hepatic microsomal enzymes cytochrome P450 (CYP1A2 or CYP3A4) responsible for lidocaine metabolism, no clinical evidence of infection, and a negative urine pregnancy test. Prospective subjects had to first request liposuction before being informed of the opportunity to participate in this research. Participants were offered liposuction at no charge.

Individual subjects served as their own controls. Large volume (≥500 mL) tumescent infiltration was accomplished using a peristaltic tumescent infiltration pump (HKSurgical.com, San Clemente, Calif.). Subcutaneous tumescent infiltration was initiated by briefly using a spinal needle (20 gauge×8.5 cm) to infiltrate a relatively small volume of tumescent lidocaine solution sufficient to allow subsequent painless insertion of blunt-tipped (16 gauge×15 cm) multi-orifice tumescent infiltration cannulas.

The anatomic area targeted for infiltration was constant for each subject. These areas, which varied among subjects, included abdomen, outer thigh, hips, back, inner thighs and knees, and female breasts. To minimize the chronotropic effects of epinephrine, most patients received oral clonidine 0.1 mg before tumescent infiltration. Clonidine (0.1 mg) and/or lorazepam (1 mg) by mouth 15 minutes before infiltration counteracted the tachycardia associated with epinephrine and provided mild anxiolysis and sedation. No narcotic analgesia or parenteral sedation was used. Prophylactic atropine, 0.3 mg IV or IM was administered to subjects with a history of syncope or near-syncope.

Each tumescent lidocaine infiltration procedure was followed by sequential serum lidocaine samples and clinical status evaluations at times T=0, 2, 4, 6, 8, 10, 12, 14, 16, 18, and 24 hours beginning immediately upon completion of infiltration.

For the 24 hours after infiltration, whenever serum samples were obtained, the awake patients were evaluated for any unpleasant subjective symptoms or signs of mild toxicity, including: lightheadedness, perioral numbness or nausea, tinnitus, blurred vision, nystagmus, ataxia, slurred speech, or confusion.

Patient monitoring during the first 12 to 14 hours included continuous cardiac rhythm, heart rate, pulse oximetry, and automatic arterial blood pressure. Heart rates, before, during, and after tumescent infiltration and immediately after liposuction were compared.

Serum samples were obtained from a peripheral vein using an indwelling 20-gauge IV catheter by a 2-syringe sampling technique. The first syringe contained 2 mL saline to flush the IV catheter and then remove and discard 2 mL of blood. Next, 10 mL blood was collected in a second syringe for assay of lidocaine by high-performance liquid chromatography by NMS Labs, Willow Grove, Pa. (Hill J, Roussin A, Lelorier J, Caille G. High-pressure liquid chromatographic determination of lidocaine and its active deethylated metabolites. J Pharm Sci 1980; 69:1341-3. The catheter was then flushed with 1 mL heparin 10 USP units per milliliter.

For each subject, the initial infiltration procedures were done without subsequent liposuction, and the final tumescent infiltration was followed by liposuction after allowing at least 1 hour of detumescence for gradual dispersion of subcutaneous tumescent fluid. Tumescent infiltration procedures were separated by at least 1 week. The liposuction aspirate was collected in clear plastic volumetric canisters. After allowing at least 1 hour for gravitational separation of the lipid and aqueous aspirate, the resulting supernatant fat, infranatant blood-tinged tumescent anesthetic solution, and the total aspirate volume were recorded.

Serum lidocaine concentrations as a function of time, Cmax, the time when Cmax occurred (Tmax), and Cmax as a function of milligram per kilogram dosage of lidocaine were determined. Area under the curve (AUC∞) of serum lidocaine concentration-time profile was calculated by the trapezoid method. AUC∞, Cmax, and Tmax without and with liposuction were compared by the paired t test.

In some individual subjects, the lidocaine concentration (mg/L) in the TLA solutions and the lidocaine dosage (mg/kg) varied between procedures to achieve a targeted milligram per kilogram dosage of lidocaine and to have sufficient volume of TLA solution to accomplish liposuction of the area.

The choices of the milligram per kilogram dosages used in the present research were motivated by clinical experience with tumescent liposuction totally by local anesthesia. Worldwide experience with tumescent liposuction has shown that 45 mg/kg with liposuction is quite safe. Without liposuction, the range of safe dosages is not known.

The Cmax following 35 mg/kg without liposuction in the first 2 subjects was well below the toxic threshold of 6 µg/mL. These results provided pharmacokinetic assurance that 45 mg/kg without liposuction would not represent a significant risk of harm to the subjects.

To achieve an adequate range of input data for linear regression analysis, some of the subjects who received 45 mg/kg without liposuction also received 22.5 mg/kg (half of 45 mg/kg) in the second study without liposuction.

Statistical Analysis

We analyzed the data. The effect of liposuction on the systemic bioavailability of subcutaneous tumescent lidocaine was assessed by pairwise comparison of AUC∞s (paired t test) among subjects whose individual dosages of tumescent lidocaine were the same without and with liposuction.

To assure statistical independence of these observations when comparing AUC∞ without and with liposuction, if a subject had 2 tumescent infiltration procedures without liposuction, then only 1 AUC∞ measurement was used in the paired t test. When these 2 lidocaine doses without liposuction were not equal, then we chose the dose that was the same as the dose with liposuction. If a subject's 2 tumescent lidocaine doses without liposuction both equaled the dosage with liposuction, then we chose the smaller AUC∞ without liposuction. Because liposuction removes lidocaine before it can be absorbed systemically, the AUC∞ without liposuction is likely to be larger than the AUC∞ with liposuction. The choice of the smaller AUC∞ without liposuction was conservative, in the sense that it reduced the likelihood that the paired t test comparing AUC∞ without and with liposuction would incorrectly detect a significant difference between a subject's AUC∞s (type I error).

For linear regression analysis of Cmax as a function of milligram per kilogram lidocaine dosage, only 1 of the 2 dosages without liposuction was used to assure statistical independence of observations. When the milligram per kilogram doses of lidocaine without liposuction were not equal, then the smallest of the 2 doses of lidocaine was used in the linear regression analysis to maximize the range of milligram per kilogram doses. When the milligram per kilogram doses of lidocaine without liposuction were equal, then the largest of the 2 Cmax values was chosen. The choice of the larger Cmax is conservative, in the sense that it increased the estimated probability that any given milligram per kilogram dose would produce a Cmax ≥6 µg/mL.

We used tolerance interval analysis to estimate the probability that a future milligram per kilogram dosage of tumescent lidocaine given to an individual would result in a Cmax ≥6 µg/mL (Krishnamoorthy K, Mathew T. Statistical Tolerance Regions. Hoboken, N.J.: John Wiley & Sons, Inc., 2009; Hahn G, Meeker W Q. Statistical Intervals: A Guide for Practitioners. John Wiley & Sons, Inc., 1991; and Myhre J, Jeske D R, Rennie M, Bi Y. Tolerance intervals in a heteroscedastic linear regression context with applications to Aerospace equipment surveillance. International J Quality Statistics Reliability 2009; 2009:Article ID 126283, 8 pages). Tolerance intervals were calculated at a 99% level of confidence.

Supplemental Digital Content 1 (http://links.lww.com/AA/B335) contains safety tips, and information regarding clinical lidocaine toxicity, case reports of tumescent lidocaine toxicity, tumescent lidocaine pharmacokinetics, formulation of TLA solution, tumescent infiltration techniques, detumescence, technique for calculating AUC∞, tolerance intervals, and R-Code to compute tolerance intervals.

Supplemental Digital Content 2 (http://links.lww.com/AA/B336) is a video of the technique for painless subcutaneous infiltration of large volumes of tumescent lidocaine.

Results

There were 41 TLA infiltration procedures. With 1 exception, all subjects had at least 2 tumescent infiltration procedures without subsequent liposuction and then 1 infiltration followed by liposuction. A single subject participated in only 1 TLA infiltration procedure without liposuction. All but 1 subject received the same milligram per kilogram dose of lidocaine at least once without liposuction and once with liposuction. The lidocaine concentration-time profile for each of the 14 subjects is shown in FIG. 1. No subject experienced a peak serum lidocaine concentration larger than 4.4 µg/mL. Tables 1 and 2 present lidocaine dosage data, without and with liposuction, respectively.

TABLE 1

Demographic Data Without Liposuction

| Patient no.-study no. | Body area | Lido (mg/bag) | Epi (mg/L) | Clonidine (mg) | Atropine (mg) | Wt (kg) | Ht (m) | $m^2$ | Lido (mg) | Lido (mg/kg) | BMI (kg/m2) | Cmax | Tmax | AUC∞ |
|---|---|---|---|---|---|---|---|---|---|---|---|---|---|---|
| 01-1 | H-OT | 700 | 1 | 0 | 0.3 | 59.7 | 1.59 | 2.53 | 2100 | 35.1 | 23.6 | 3.3 | 10 | 54.5 |
| 01-2 | H-OT | 700 | 0.5 | 0 | 0.3 | 59.7 | 1.59 | 2.53 | 2100 | 35.1 | 23.6 | 3.4 | 8 | 57.7 |
| 02-1 | I(T/K) | 700 | 1 | 0 | 0 | 62.1 | 1.68 | 2.81 | 1956 | 31.4 | 22.1 | 1.9 | 8 | 29.4 |
| 02-2 | I(T/K) | 700 | 0.5 | 0 | 0 | 62.6 | 1.68 | 2.81 | 1956 | 31.2 | 22.3 | 2.1 | 10 | 35 |
| 03-1 | H-F | 1000 | 1 | 0 | 0 | 83.6 | 1.78 | 3.17 | 3782 | 45.2 | 26.4 | 4.1 | 12 | 61.5 |
| 03-2 | Rt:H-F | 1000 | 1 | 0 | 0 | 82.7 | 1.78 | 3.17 | 2073 | 25.1 | 26.1 | 2.7 | 11 | 42 |
| 04-1 | H-OT | 1000 | 1 | 0.1 | 0 | 70.2 | 1.625 | 2.64 | 3159 | 45 | 26.6 | 3.5 | 14 | 57.9 |
| 04-2 | H-OT | 1000 | 0.5 | 0.1 | 0 | 70.2 | 1.625 | 2.64 | 3171 | 44.9 | 26.6 | 3.6 | 16 | 59 |
| 05-1 | H-OT | 800 | 1 | 0.1 | 0 | 74.8 | 1.75 | 3.06 | 3375 | 45 | 24.5 | 2.2 | 18 | 44.5 |
| 05-2 | H-OT | 800 | 1 | 0.1 | 0 | 75.5 | 1.75 | 3.06 | 3406 | 45 | 24.7 | 3.2 | 14 | 60.5 |
| 06-1 | H-OT | 1000 | 1 | 0.1 | 0.3 | 68.5 | 1.69 | 2.85 | 3090 | 45 | 24 | 2.9 | 8 | 44.4 |
| 06-2 | H-OT | 1000 | 1 | 0.1 | 0.3 | 68.6 | 1.69 | 2.85 | 1539 | 22.5 | 24.1 | 1.4 | 12 | 21 |
| 07-1 | Abd | 1000 | 1 | 0.1 | 0 | 64.9 | 1.72 | 2.96 | 2514 | 38.7 | 21.9 | 1.9 | 10 | 33.4 |
| 07-2 | Abd | 1000 | 0.5 | 0.1 | 0 | 65.3 | 1.72 | 2.96 | 2531 | 38.7 | 22.1 | 2.7 | 10 | 44.3 |
| 08-1 | 2 OT, I(T/K) | 1000 | 1 | 0 | 0 | 55.9 | 1.67 | 2.79 | 2516 | 45 | 20 | 4.3 | 12 | 52.7 |
| 08-2 | 1 OT, I(T/K) | 1000 | 1 | 0 | 0 | 54.1 | 1.67 | 2.79 | 1217 | 22.5 | 19.4 | 1.9 | 10 | 26 |
| 09-1 | Abd | 1000 | 1 | 0.1 | 0 | 70.76 | 1.6 | 2.56 | 3189 | 45 | 27.6 | 3.6 | 14 | 70.3 |
| 09-2 | Abd | 1000 | 1 | 0.1 | 0 | 70.76 | 1.6 | 2.56 | 3189 | 45 | 27.6 | 4.2 | 16 | 70.8 |
| 10-1 | L Brst | 1000 | 1 | 0.1 | 0 | 100 | 1.73 | 2.99 | 2018 | 20 | 33.4 | 1.2 | 14 | 25.6 |
| 10-2 | L Brst | 1000 | 1 | 0.1 | 0 | 100 | 1.73 | 2.99 | 2028 | 20 | 33.4 | 1.6 | 24 | 26.9 |
| 11-1 | L Brst | 1000 | 1 | 0.1 | 0 | 79.1 | 1.65 | 2.72 | 1522 | 19.2 | 29.1 | 1.6 | 14 | 24.2 |
| 11-2 | L Brst | 1000 | 1 | 0.1 | 0 | 80 | 1.65 | 2.72 | 1549 | 19.4 | 29.4 | 1.4 | 14 | 21.8 |
| 12-1 | Abd | 1000 | 1 | 0 | 0 | 80.7 | 1.575 | 2.48 | 3640 | 45 | 32.5 | 4.3 | 16 | 62 |
| 12-2 | Abd | 1000 | 1 | 0 | 0 | 81 | 1.575 | 2.48 | 3651 | 45 | 32.7 | 4.4 | 18 | 77.4 |
| 13-2 | H-OT | 1000 | 1 | 0 | 0 | 66.4 | 1.63 | 2.66 | 2957 | 44.5 | 25 | 3.7 | 10 | 48.3 |
| 14-1 | H-OT | 1000 | 1 | 0 | 0.3 | 76.4 | 1.75 | 3.06 | 3436 | 45 | 25 | 3.4 | 16 | 49.6 |
| 14-2 | H-OT | 1000 | 1 | 0 | 0.3 | 76.4 | 1.75 | 3.06 | 1718 | 22.5 | 25 | 1.8 | 14 | 26.5 |

The weight and height for each of the 14 subjects and the drug and dosage data for each of the 27 research studies including peak serum concentration (Cmax), time at Cmax (Tmax), and area under the curve of the serum lidocaine concentration-time profile (AUC∞) are given. Abd = abdomen; BMI = body mass index; Epi = epinephrine; H-F = hips and flanks/back; Ht = height; H-OT = hips and outer thighs; I(T/K) = inner thighs and knees; L Brst = left breast; Lido = lidocaine; Wt = weight.

TABLE 2

Demographic Data with Liposuction

| Patient no.-study no. | Area | Lido (mg/bag) | Epi (mg/bag) | Clonidine (mg) | Atropine (mg) | Wt (kg) | Ht (m) | $m^2$ | Lido (mg) | Lido (mg/kg) | BMI |
|---|---|---|---|---|---|---|---|---|---|---|---|
| 01-3 | H-OT | 700 | 1 | 0 | 0.3 | 59.7 | 1.59 | 2.53 | 2074 | 34.7 | 23.6 |
| 02-3 | 1(T/K) | 700 | 1 | 0 | 0 | 63 | 167.7 | 2.81 | 1984 | 31.4 | 22.4 |
| 03-3 | H-F | 1000 | 1 | 0 | 0 | 83.6 | 1.78 | 3.17 | 3900 | 46.7 | 26.3 |
| 04-3 | H-OT | 1000 | 1 | 0.1 | 0 | 70.2 | 1.625 | 2.64 | 3159 | 52 | 26.6 |
| 05-3 | H-OT | 800 | 1 | 0.1 | 0 | 75.5 | 1.75 | 3.06 | 3405 | 45 | 24.7 |
| 06-3 | H-OT | 1000 | 1 | 0.1 | 0.3 | 69.1 | 1.69 | 2.85 | 3190 | 46.1 | 24.2 |
| 07-3 | Abd | 1000 | 1 | 0.1 | 0 | 66.2 | 1.72 | 2.96 | 2550 | 38.4 | 22.4 |
| 08-3 | OT, I(T/K) | 1000 | 1 | 0 | 0.3 | 55.2 | 1.67 | 2.79 | 2516 | 45.6 | 19.8 |
| 09-3 | Abd | 1000 | 1 | 0.1 | 0 | 71.2 | 1.6 | 2.56 | 3318.6 | 46.6 | 27.8 |
| 10-3 | 2Brst | 1000 | 1 | 0.1 | 0 | 101 | 1.73 | 2.99 | 4122 | 40.5 | 33.8 |
| 11-3 | L Brst | 1000 | 1 | 0.1 | 0 | 81.1 | 1.65 | 2.72 | 1572 | 19.4 | 29.8 |
| 12-3 | Abd | 1000 | 1 | 0.1 | 0 | 81.7 | 1.575 | 2.48 | 3674 | 45 | 32.9 |
| 13-2 | H-OT | 1000 | 1 | 0 | 0 | 66.4 | 1.63 | 2.66 | 2993 | 45.7 | 25 |
| 14-3 | H-OT | 1000 | 1 | 0.1 | 0.3 | 76.4 | 1.75 | 3.06 | 3436 | 45 | 25 |

| Patient no.-study no. | Cmax | Tmax | AUC∞ | Aspirate (mL) | Supranat (mL) | Infranat (mL) |
|---|---|---|---|---|---|---|
| 01-3 | 2.5 | 8 | 35.3 | 1950 | 1750 | 200 |
| 02-3 | 2.1 | 10 | 31 | 1100 | 750 | 350 |
| 03-3 | 4.2 | 10 | 48.6 | 1900 | 1250 | 650 |
| 04-3 | 2.8 | 12 | 40.6 | 2425 | 2000 | 425 |
| 05-3 | 1.7 | 16 | 27.6 | 2220 | 1845 | 525 |
| 06-3 | 1.8 | 12 | 33.7 | 2080 | 1840 | 240 |
| 07-3 | 1.7 | 14 | 31.9 | 1300 | 950 | 350 |
| 08-3 | 2.3 | 12 | 34.8 | 1525 | 1395 | 130 |
| 09-3 | 2.4 | 14 | 33.8 | 2700 | 1875 | 825 |

TABLE 2-continued

Demographic Data with Liposuction

| 10-3 | 2.7  | 16 | 37.7 | 2500 | 1450 | 1050 |
|------|------|----|------|------|------|------|
| 11-3 | 0.97 | 18 | 15.2 | 700  | 450  | 250  |
| 12-3 | 3.8  | 12 | 67.8 | 2800 | 2260 | 540  |
| 13-2 | 2.8  | 8  | 33   | 2550 | 2200 | 350  |
| 14-3 | 2.7  | 10 | 35.7 | 3300 | 2900 | 400  |

The weight and height for each of the 14 subjects and the drug and dosage data for each of the 14 research studies including peak serum concentration (Cmax), time at Cmax (Tmax), area under the curve of the serum lidocaine concentration-time profile (AUC∞) are given. Abd = abdomen; BMI = body mass index; Epi = epinephrine; H-F = hips and flanks/back; H-OT = hips & and outer thighs; Ht = height; Infranat = infranatant; I(T/K) = inner thighs and knees; L Brst = left breast; Lido = lidocaine; Supranat = supernatant; Wt = weight.

Without liposuction, the range of lidocaine content in bags of tumescent solution was 700 to 1000 mg/bag. With liposuction, the range of lidocaine content was 770 to 1000 mg/bag. The ranges of milligram per kilogram dosages of lidocaine were 19.2 to 45.0 mg/kg without liposuction and 19.4 to 52 mg/kg with liposuction. Ten subjects received 45 mg/kg without liposuction and at least 45 mg/kg with liposuction. The total milligram dose of tumescent lidocaine ranged from 1800 mg to 3600 mg. During this research, the volume of infiltrated TLA solution ranged from 2 to 4 L. Subjects received no IV fluids, no systemic sedatives, and no narcotic analgesics.

Among those who received 45 mg/kg tumescent lidocaine for liposuction, the mean total volume of aspirate was 2416 mL (range, 1525-3300 mL), mean volume of supernatant fat was 1863 mL (range, 1250-2900 mL), and mean volume infranatant blood-tinged anesthetic solution was 553 mL (range, 130-1100 mL).

Figure 2:
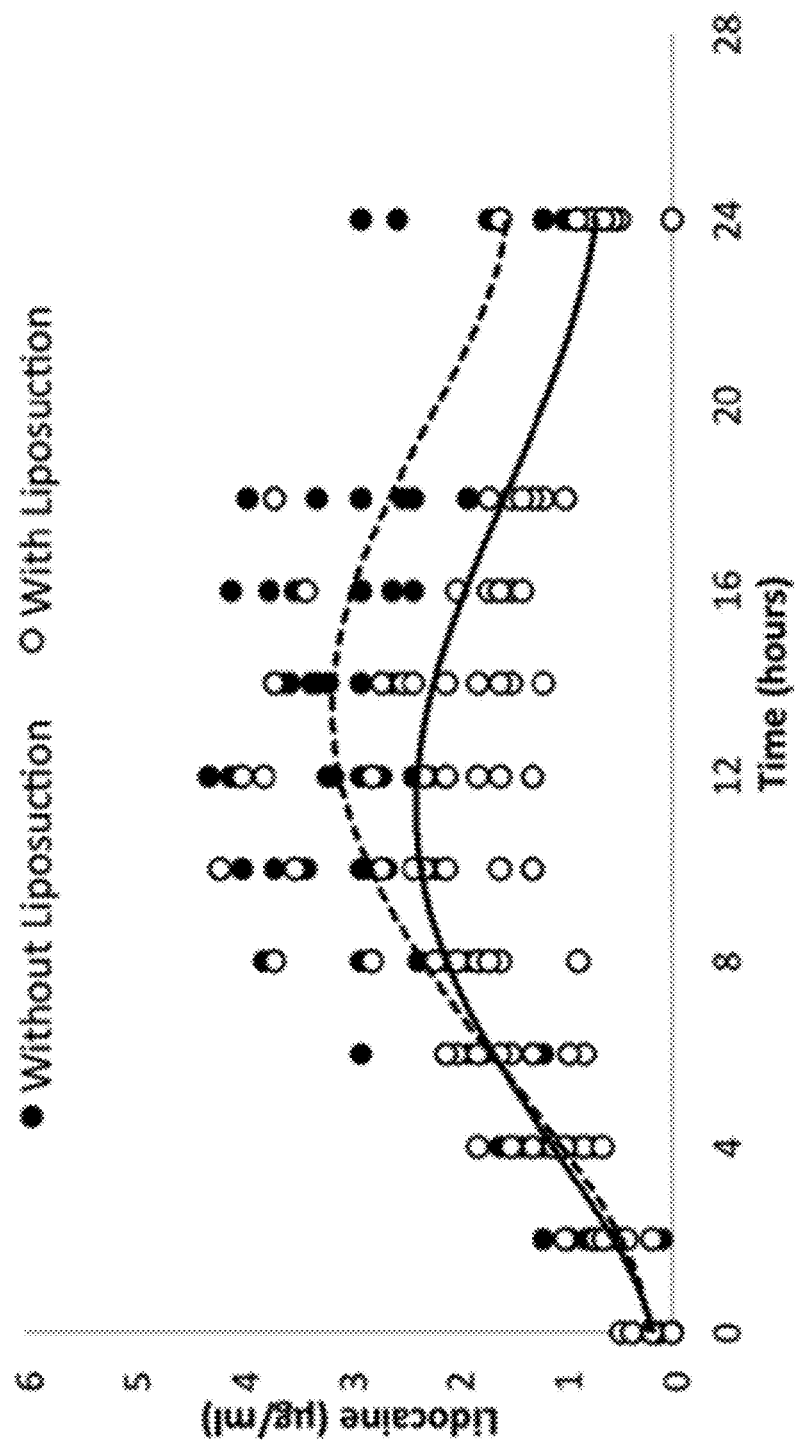
FIG. 2. Comparison of serum lidocaine concentrations at sequential times over 24 h following 45 mg/kg tumescent lidocaine, without liposuction (closed circles) and with liposuction (open circles). The AUC∞ of the mean concentrations (solid line) at each time point without liposuction (56.2 µg·h/mL) is 28% greater than the AUC∞ of the mean concentrations (dashed line) with liposuction (40.7 µg·h/mL).

At equal milligram per kilogram dosages of tumescent lidocaine without and with liposuction, the mean AUC∞ for serum lidocaine concentration-time profile without liposuction (56.2 μg·h/mL) was significantly higher than that with liposuction (40.7 μg·h/mL; P=0.001). As presented in FIG. 2, liposuction removed approximately 28% of the lidocaine before it could be absorbed into the systemic circulation.

At equal milligram per kilogram dosages of tumescent lidocaine, the mean Cmax without liposuction 2.9 μg/mL (range, 1.2-4.4) was significantly higher than the mean Cmax with liposuction 2.38 μg/mL (range, 0.97-3.8) by the paired t test (P=0.001). The mean Tmax without liposuction was 13.1 hours (range, 8-24), which was not significantly different from the mean Tmax with liposuction 12.5 hours (range, 8-18; P=0.19).

Without liposuction, the dose of epinephrine ranged from 1.2 to 4.3 mg and the mean difference in heart rate before and after infiltration was −3.4 (range, −24 to +17). With liposuction, the dose of epinephrine ranged from 1.6 to 4.3 mg, and the difference in heart rate before infiltration and after liposuction was not significant (P=0.13; mean=+5; range, −12 to +33).

One subject who was relatively thin, with body mass index of 20, received 45 mg/kg without liposuction, which produced a Cmax of 4.3 μg/mL and experienced transient nausea approximately 12 hours after infiltration. There were no other lidocaine-associated adverse events.

There was no clinical evidence of epinephrine toxicity, such as chest pain or discomfort, dyspnea, dizziness, headache, anxiety, nervousness, restlessness, tremors, diaphoresis, pallor, rapid, irregular or pounding heart rate, or pounding in the ears.

There were no observed signs or symptoms of neurotoxicity, syncope, and near-syncope. There was no evidence of cardiac toxicity, such as arrhythmia, tachycardia, bradycardia, hypertension, hypotension, volume overload heart failure, pulmonary edema, or hypoxia.

Figure 3:
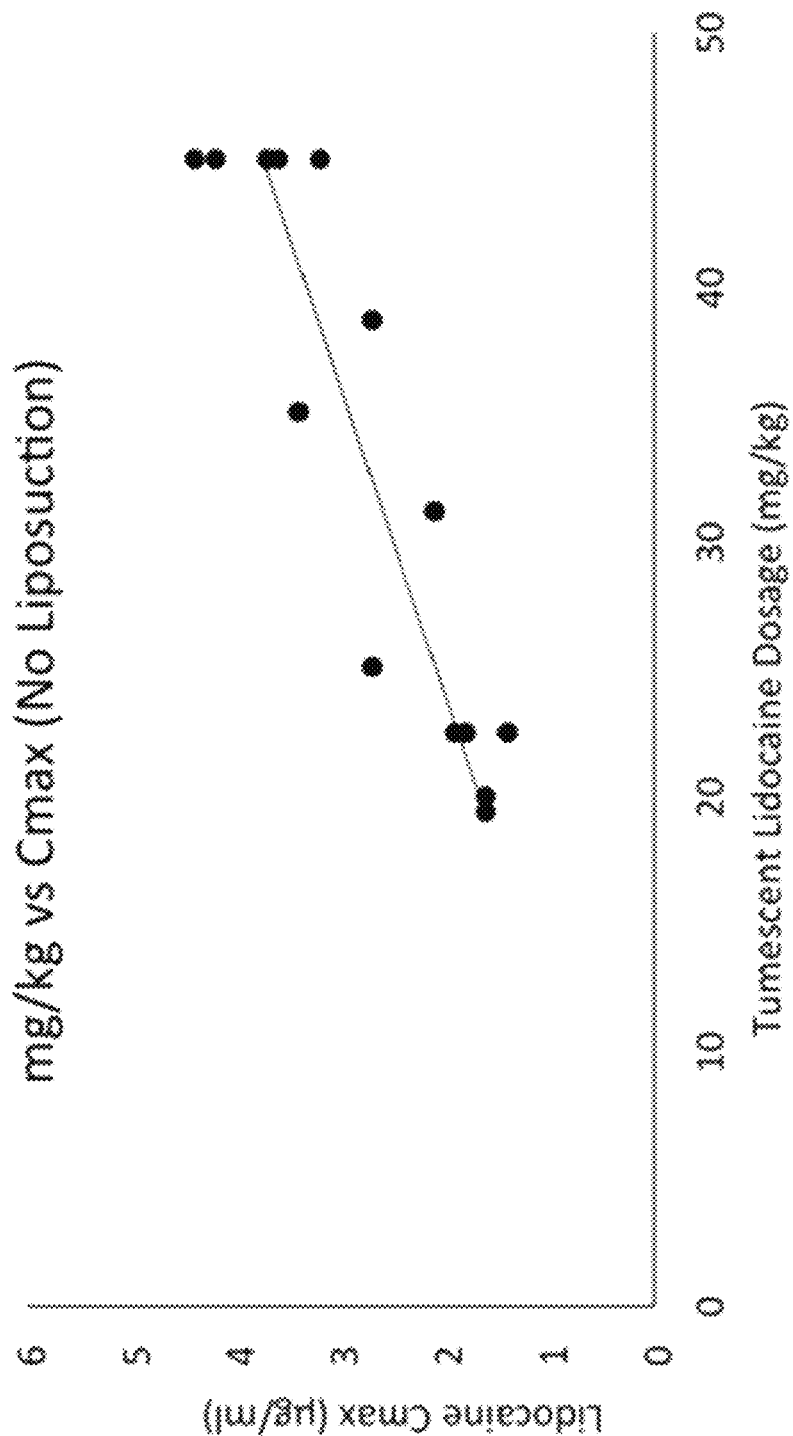
FIG. 3. Scatter plot of tumescent lidocaine dosage versus peak serum lidocaine concentrations (Cmax) without liposuction. The solid line represents the line of regression with a coefficient of determination ($R^2$) of 0.85.
Figure 4:
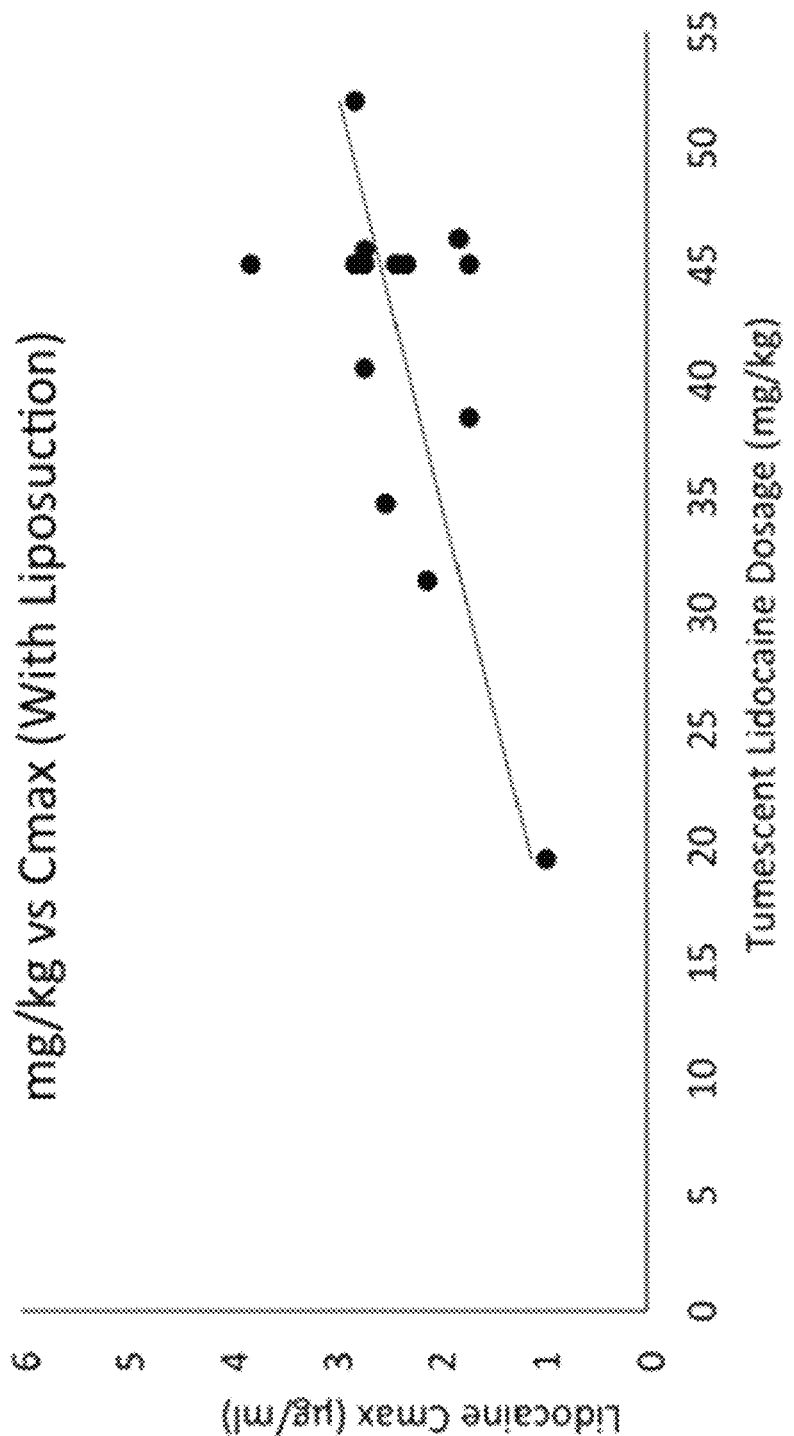
FIG. 4. Scatter plot of tumescent lidocaine dosage versus peak serum lidocaine concentrations (Cmax) with liposuction. The solid line represents the line of regression with a coefficient of determination ($R^2$) of 0.35.
Figure 5:
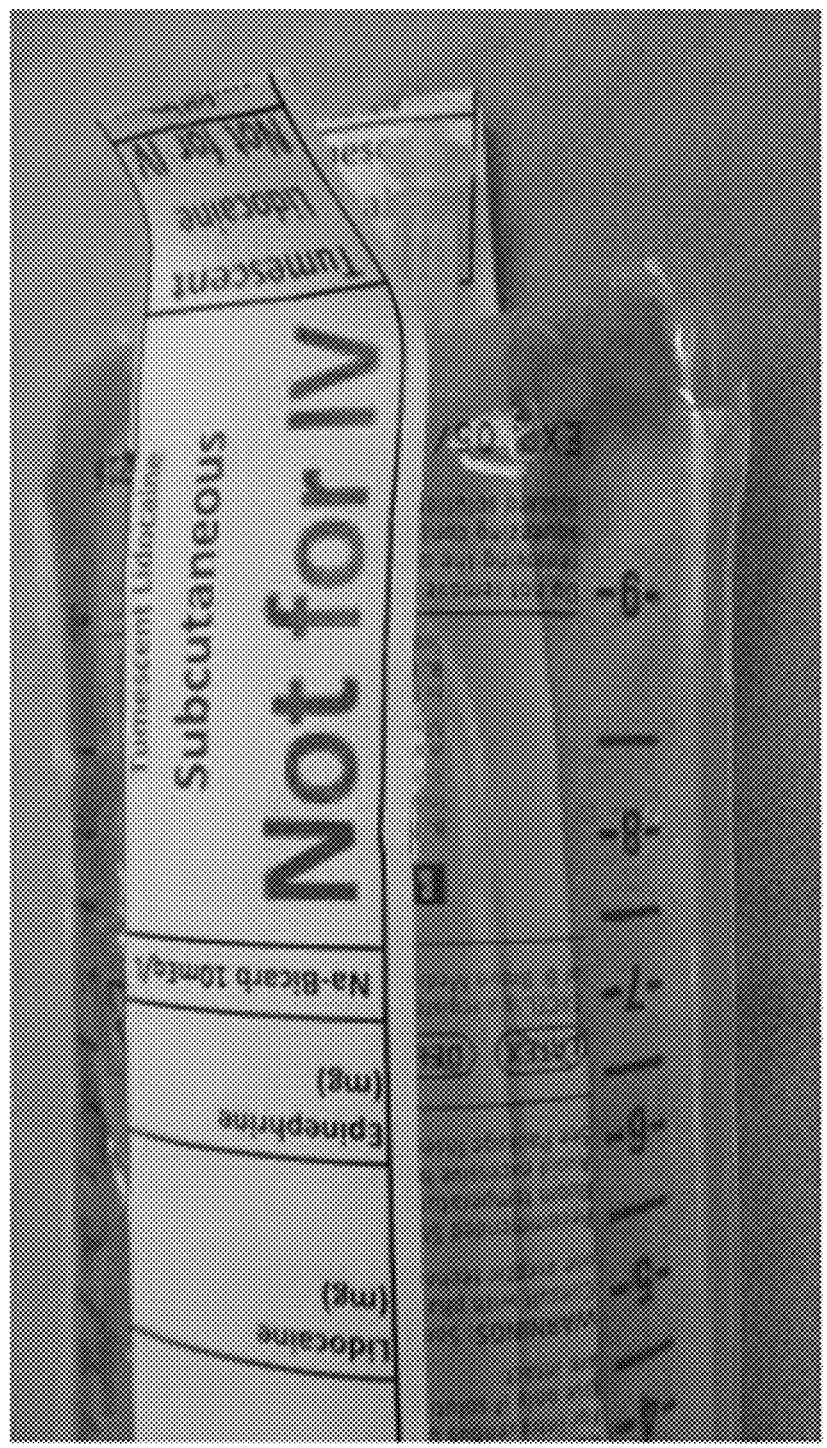
FIG. 5. "Safety Label" applied to a bag tumescent lidocaine solution. The label overhangs the port for the IV tubing spike. A "Safety Label" is a visual reminder that the bag contains tumescent lidocaine for subcutaneous delivery and is not for IV delivery.

Without liposuction, there was a strong linear relationship between milligram per kilogram dosage of tumescent lidocaine and Cmax ($R^2$=0.85; FIG. 3). With liposuction, there was a weaker linear relationship between milligram per kilogram dosage of tumescent lidocaine and Cmax ($R^2$=0.36; see FIG. 4).

Based on the tolerance interval analysis, the estimated probability that a future milligram per kilogram dose of tumescent lidocaine given to an individual would result in a Cmax ≥6 μg/mL is shown in Table 3.

TABLE 3

Risk of Lidocaine Serum Concentration >6 μg/mL
(99% Confidence)

| | Dosage of tumescent lidocaine (mg/kg) | | | | | | |
|---|---|---|---|---|---|---|---|
| | 21 | 28 | 35 | 40 | 45 | 50 | 55 |
| No liposuction | <1/10$^{16}$ | 1/5 × 10$^6$ | 1/10,000 | 1/750 | 1/80 | 1/15 | 1/4 |
| With liposuction | 1/5 × 10$^{10}$ | 1/2 × 10$^7$ | 1/2 × 10$^5$ | 1/15,000 | 1/2000 | 1/500 | 1/100 |

Estimated probabilities that any given dosage milligram per kilogram dosage will result in a peak serum lidocaine concentration (Cmax) ≥6 μg/mL, the threshold for mild lidocaine toxicity, were derived from tolerance interval analysis with a 99% level of confidence.

Supplemental Digital Content 3 (available on the internet at: links.lww.com/AA/B337) presents patient-level raw data and additional analysis including tables in comma-separated values (cvs) format.

Discussion

Our findings confirmed our main hypothesis that doses of TLA that are far larger than the current FDA limit of 7 mg/kg are a nonsignificant risk of harm to patients.

After the subcutaneous infiltration of tumescent lidocaine, we observed the serum concentration-time profiles without and with liposuction and found that tumescent lidocaine absorption continues beyond 24 hours. For a given dosage of a drug, prolonging its systemic absorption reduces its Cmax.

This explains the remarkable safety of large dosages of tumescent lidocaine and epinephrine.

At equal doses of tumescent lidocaine, the average AUC∞ of the concentration-time profiles is 28% smaller with liposuction than it is without liposuction. This supports our hypothesis that liposuction removes a significant amount of subcutaneous tumescent lidocaine before it can be absorbed into the circulation. Thus, data derived from liposuction patients cannot be used to estimate the maximal safe milligram per kilogram dosage of tumescent lidocaine without liposuction.

Furthermore, these concentration-time profiles resemble the profile of a constant IV lidocaine infusion that is discontinued at Tmax. There is a growing literature indicating that systemic IV lidocaine may have beneficial perioperative effects, including preemptive analgesia, reduced postoperative narcotic requirements, and reduced systemic inflammatory response to surgical trauma (Garutti I, Rancan L, Simon C, Cusati G, Sanchez-Pedrosa G, Moraga F, Olmedilla L, Lopez-Gil M T, Vara E. Intravenous lidocaine decreases tumor necrosis factor alpha expression both locally and systemically in pigs undergoing lung resection surgery. Anesth Analg 2014; 119:815-28; De Oliveira G S Jr, Fitzgerald P, Streicher L F, Marcus R J, McCarthy R J. Systemic lidocaine to improve postoperative quality of recovery after ambulatory laparoscopic surgery. Anesth Analg 2012; 115: 262-7; Piegeler T, Votta-Velis E G, Liu G, Place A T, Schwartz D E, Beck-Schimmer B, Minshall R D, Borgeat A. Antimetastatic potential of amide-linked local anesthetics: inhibition of lung adenocarcinoma cell migration and inflammatory Src signaling independent of sodium channel blockade. Anesthesiology 2012; 117:548-59; McKay A, Gottschalk A, Ploppa A, Durieux M E, Groves D S. Systemic lidocaine decreased the perioperative opioid analgesic requirements but failed to reduce discharge time after ambulatory surgery. Anesth Analg 2009; 109:1805-8; de Klaver M J, Buckingham M G, Rich G F. Lidocaine attenuates cytokine-induced cell injury in endothelial and vascular smooth muscle cells. Anesth Analg 2003; 97:465-70; McCarthy G C, Megalla S A, Habib A S. Impact of intravenous lidocaine infusion on postoperative analgesia and recovery from surgery: a systematic review of randomized controlled trials. Drugs 2010; 70:1149-63; Wang H L, Zhang WH, Lei W F, Zhou C Q, Ye T. The inhibitory effect of lidocaine on the release of high mobility group box 1 in lipopolysaccharide-stimulated macrophages. Anesth Analg 2011; 112:839-44; and Kaczmarek D J, Herzog C, Larmann J, Gillmann H J, Hildebrand R, Schmitz M, Westermann A, Harendza T, Werdehausen R, Osthaus A W, Echtermeyer F, Hahnenkamp K, Wollert K C, Theilmeier G. Lidocaine protects from myocardial damage due to ischemia and reperfusion in mice by its antiapoptotic effects. Anesthesiology 2009; 110:1041-9). The observation that tumescent infiltration produces a concentration-time profile similar to a constant IV infusion of lidocaine suggests a new hypothesis, to be tested in the future, that local TLA may have desirable systemic effects.

During each of the 41 studies, we observed heart rate, arterial blood pressure, pulse oximetry, and cardiac rhythm and inquired about any subjective symptoms suggestive of lidocaine toxicity. There were no episodes of tachycardia although most patients did receive oral clonidine (0.1 mg) for its anxiolytic effect and to counteract the positive chronotropic effects of epinephrine. One patient encountered a brief episode of nausea at 45 mg/kg without liposuction. The data indicates that without liposuction 45 mg/kg is risky, while 28 mg/kg is a more reasonable maximal safe dosage. Otherwise, careful observation of patients over the course of 41 pharmacokinetic studies revealed no adverse events associated with the systemic effects of lidocaine and epinephrine. This finding confirmed our hypothesis that adverse events associated with the large dosages of tumescent lidocaine with epinephrine are infrequent.

The association between the milligram per kilogram dosage of tumescent lidocaine and the subsequent peak serum lidocaine concentrations (Cmax) was analyzed both without and with liposuction. The data confirmed our hypothesis that there is a close linear relationship between the milligram per kilogram dosage of tumescent lidocaine without liposuction and Cmax. Thus, an increased milligram per kilogram dosage of tumescent lidocaine is associated with an increased risk of toxicity.

Liposuction removes lidocaine before it can be absorbed and thus reduces the correlation between the milligram per kilogram dosage of tumescent lidocaine liposuction and Cmax. With liposuction, an estimate of the maximum safe dosage of tumescent lidocaine is less reliable than without liposuction. Years of worldwide experience have shown that 55 mg/kg tumescent lidocaine for liposuction is remarkably safe (Ostad A, Kageyama N, Moy R L. Tumescent anesthesia with a lidocaine dose of 55 mg/kg is safe for liposuction. Dermatol Surg 1996; 22:921-7; and Habbema L. Safety of liposuction using exclusively tumescent local anesthesia in 3,240 consecutive cases. Dermatol Surg 2009; 35:1728-35). This dosage is safe most of the time. Multiple large surveys involving thousands of procedures have found no evidence of tumescent lidocaine toxicity at recommended dosages (Coldiron B M, Healy C, Bene N I. Office surgery incidents: what seven years of Florida data show us. Dermatol Surg 2008; 34:285-91; Grazer F M, de Jong R H. Fatal outcomes from liposuction: census survey of cosmetic surgeons. Plast Reconstr Surg 2000; 105:436-46; and Lehnhardt M, Homann H H, Daigeler A, Hauser J, Palka P, Steinau H U. Major and lethal complications of liposuction: a review of 72 cases in Germany between 1998 and 2002. Plast Reconstr Surg 2008; 121:396e-403e). However, 55 mg/kg may be too risky if lidocaine absorption is too rapid (failure to add epinephrine to the solution of tumescent lidocaine) or if lidocaine metabolism is too slow (diabetes (Moises E C, Duarte Lde B, Cavalli Rde C, Marques M P, Lanchote V L, Duarte G, da Cunha S P. Pharmacokinetics of lidocaine and its metabolite in peridural anesthesia administered to pregnant women with gestational diabetes mellitus. Eur J Clin Pharmacol 2008; 64:1189-96) adverse interactions with drugs that inhibit the hepatic microsomal isoenzymes cytochrome P450 3A4 and 1A2 such as erythromycin (Olkkola K T, Isohanni M H, Hamunen K, Neuvonen P J. The effect of erythromycin and fluvoxamine on the pharmacokinetics of intravenous lidocaine. Anesth Analg 2005; 100: 1352-6) sertraline, fluconazole or ciprofloxacin, propofol (Yang L Q, Yu W F, Cao Y F, Gong B, Chang Q, Yang G S. Potential inhibition of cytochrome P450 3A4 by propofol in human primary hepatocytes. World J Gastroenterol 2003; 9:1959-62) or general anesthesia (Copeland S E, Ladd L A, Gu X Q, Mather L E. The effects of general anesthesia on whole body and regional pharmacokinetics of local anesthetics at toxic doses. Anesth Analg 2008; 106:1440-9) or if patients have very low serum protein concentrations or if surgery is cancelled before liposuction can be completed. Based on the present data and considerable worldwide experience, we believe that 45 mg/kg is a safe and prudent maximum dosage of tumescent lidocaine for liposuction. Furthermore, 45 mg/kg is less likely than 55 mg/kg to permit excessive amounts of liposuction.

Tolerance interval analysis was used to calculate the proportion of individuals who, when given a specified milligram per kilogram dosage of tumescent lidocaine, will have a Cmax exceeding 6 μg/mL. The results confirmed our hypothesis that dosages larger than 7 mg/kg are associated with a risk of <1/1000 for mild lidocaine toxicity. In particular, without liposuction, a dosage of 45 mg/kg has an estimated risk of mild toxicity of 1/80 and at 28 mg/kg the estimated risk of mild toxicity was several orders of magnitude <1/2000. With liposuction, a dosage of 45 mg/kg has an estimated risk of mild toxicity of 1/2000. Thus, the risk of mild toxicity at 28 mg/kg without liposuction and 45 mg/kg with liposuction is each <1/1000 and can be said to represent a nonsignificant risk of harm to patients. For nonliposuction surgeries, 28 mg/kg tumescent lidocaine is a prudent choice while allowing at least 2 L tumescent solution in a 70-kg adult.

CONCLUSIONS

Within our sample of 14 subjects there was no evidence of lidocaine or epinephrine toxicity. Preliminary estimates for maximum safe dosages of tumescent lidocaine are 28 mg/kg without liposuction and 45 mg/kg with liposuction. As a result of delayed systemic absorption, these dosages yield serum lidocaine concentrations below levels associated with mild toxicity and represent a nonsignificant risk of harm to patients.

It is understood that the examples and embodiments described herein are for illustrative purposes only and that various modifications or changes in light thereof will be suggested to persons skilled in the art and are to be included within the spirit and purview of this application and scope of any appended claims. All figures, tables, and appendices, as well as publications, patents, and patent applications, cited herein are hereby incorporated by reference in their entirety for all purposes.

What is claimed is:

1. A tumescent contravenom solution comprising:
   (a) a vasoconstrictor drug,
   (b) a physiological crystalloid solution adjusted to an acidic pH; and
   (c) a contravenom agent selected from the group consisting of a protease inhibitor that counteracts a venom protease, a metalloprotease chelating agent, a phospholipase A2 inhibitor, a cellular receptor site blocker that blocks interaction of a venom protein with integrins and a contravenom agent that counters a procoagulation or a coagulation inhibitory property of a venom.

2. The tumescent contravenom solution according to claim 1, wherein the phospholipase A2 inhibitor is Varespladib or a salt thereof.

3. The tumescent contravenom solution according to claim 2, wherein the salt of Varespladib is a sodium salt.

4. The tumescent contravenom solution according to claim 1, wherein contravenom neutralizes a venom from an organism selected from the group consisting of a *Cnidarian*, a jellyfish, a sea anemone, a hydra, a mollusk, an annelid, an arthropod, a spider, a scorpion, a centipede, a bee, a wasp, an ant, a tick, a horsefly, an echinoderm, a starfish, a sea urchin, and a venomous vertebrate, including a fish, an amphibian, a snake, a lizard and a mammal.

5. The tumescent contravenom solution according to claim 1, wherein the vasoconstrictor is epinephrine.

6. The tumescent contravenom solution according to claim 5, wherein the epinephrine is at a concentration of 0.2 to 1.5 mg/L.

7. The tumescent contravenom solution according to claim 1, further comprising a drug that impairs or paralyzes lymphatic smooth muscle function and impairs lymphatic transport of venom.

8. The tumescent contravenom solution according to claim 1, further comprising a local anesthetic.

9. The tumescent contravenom solution according to claim 8, wherein the local anesthetic is lidocaine.

10. The tumescent contravenom solution according to claim 9, wherein lidocaine is at a concentration of 0.4 mg/ml to 1.2 mg/ml.

11. The tumescent contravenom solution according to claim 1, further comprising a beta-blocker drug that slows heart rate, thereby limiting systemic distribution of venom.

12. The tumescent contravenom solution according to claim 1, wherein the concentration of contravenom agent is diluted by a factor of 2 or more by the physiological crystalloid solution, or wherein a volume used to dissolve a lyophilized powder of the contravenom agent is at least twice a minimal amount required to dissolve the contravenom agent.

13. The tumescent contravenom solution according to claim 1, wherein the physiological crystalloid solution is selected from the group consisting of 0.9% physiologic saline and lactated Ringer's solution.

14. A method of treating an envenomation in a subject comprising locally injecting the tumescent contravenom solution according to claim 1 within and/or around a site of the envenomation.

15. The method according to claim 14, comprising self-administering of the tumescent contravenom solution by the subject.

16. The method according to claim 14, wherein the tumescent contravenom solution is injected subcutaneously or intramuscularly.

17. The method according to claim 14, wherein the contravenom solution is injected within 5-10 minutes following the envenomation.

18. A kit for performing the method according to claim 14 comprising:
   (a) a physiological crystalloid solution adjusted to an acidic pH,
   (b) a vasoconstrictor that is either in solid or liquid form,
   (c) a contravenom agent selected from the group consisting of a protease inhibitor that counteracts a venom protease, a metalloprotease chelating agent, a phospholipase A2 inhibitor, a cellular receptor site blocker that blocks interaction of a venom protein with integrins and a contravenom agent that counters a procoagulation or a coagulation inhibitory property of a venom;
   (c) a hypodermic needle or an infiltration cannula, and
   (d) a syringe.

19. The kit according to claim 18, further comprising a contravenom agent and/or a drug that impairs or paralyzes lymphatic smooth muscle function and impairs lymphatic transport of venom.

20. The tumescent contravenom solution according to claim 1, wherein the physiological crystalloid solution is adjusted to have a pH in the range of 3.8 to 5.0.

* * * * *